US011017216B2

(12) United States Patent
Taoka et al.

(10) Patent No.: US 11,017,216 B2
(45) Date of Patent: May 25, 2021

(54) SKIN ANALYZING DEVICE, SKIN ANALYZING METHOD, AND RECORDING MEDIUM

(71) Applicant: Panasonic Intellectual Property Management Co., Ltd., Osaka (JP)

(72) Inventors: Hiroki Taoka, Kyoto (JP); Hiroshi Matsumoto, Kanagawa (JP); Ichiro Takei, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 79 days.

(21) Appl. No.: 16/594,221

(22) Filed: Oct. 7, 2019

(65) Prior Publication Data
US 2020/0167552 A1 May 28, 2020

(30) Foreign Application Priority Data

Nov. 22, 2018 (JP) .............................. JP2018-219269

(51) Int. Cl.
*G06K 9/00* (2006.01)
*A61B 5/107* (2006.01)
(Continued)

(52) U.S. Cl.
CPC ........ *G06K 9/00302* (2013.01); *A61B 5/1079* (2013.01); *A61B 5/442* (2013.01);
(Continued)

(58) Field of Classification Search
CPC ........... G06K 9/00302; G06K 9/00281; G06K 9/3233; G06K 9/00248; A61B 5/1079;
(Continued)

(56) References Cited

U.S. PATENT DOCUMENTS 10,614,921 B2 * 4/2020 Shen ...................... G06F 3/0488
2003/0063801 A1 4/2003 Rubinstenn et al.
(Continued)

FOREIGN PATENT DOCUMENTS

| JP | 2003-187251 | 7/2003 |
| JP | 2010-086036 | 4/2010 |
| WO | 2015/015793 | 2/2015 |

OTHER PUBLICATIONS

The Extended European Search Report dated May 18, 2020 for the related European Patent Application No. 19206869.0.

*Primary Examiner* — Wesley J Tucker
(74) *Attorney, Agent, or Firm* — Greenblum & Bernstein, P.L.C.

(57) ABSTRACT

A skin analyzing device includes: a facial coordinates setting unit that sets facial coordinates on a facial image of a measurement subject by using, as a reference, a position of a facial portion identified from the facial image, a region-of-interest setting unit that sets a first region of interest to a first facial image of the measurement subject, and sets a second region of interest that has facial coordinates in common with the first region of interest to a second facial image of the measurement subject, and a skin analysis user interface (UI) unit that displays the first facial image and the second facial image next to each other, and displays a skin analysis result in the first region of interest with respect to the first facial image and a skin analysis result in the second region of interest with respect to the second facial image.

10 Claims, 28 Drawing Sheets

(51) Int. Cl.
*A61B 5/00* (2006.01)
*G06T 7/00* (2017.01)

(52) U.S. Cl.
CPC ........ *G06K 9/00281* (2013.01); *G06T 7/0012* (2013.01); *G06T 2207/30088* (2013.01); *G06T 2207/30201* (2013.01)

(58) Field of Classification Search
CPC ....... A61B 5/442; A61B 5/0077; A61B 5/748; A61B 5/441; G06T 7/0012; G06T 2207/30088; G06T 2207/30201
See application file for complete search history.

(56) References Cited

U.S. PATENT DOCUMENTS

| | | | |
|---|---|---|---|
| 2005/0169520 A1* | 8/2005 | Chen ..................... | G06T 7/0012 382/165 |
| 2009/0060290 A1* | 3/2009 | Sabe .................. | G06K 9/00248 382/118 |
| 2013/0234927 A1* | 9/2013 | Roh ........................ | G06F 3/011 345/156 |
| 2015/0186518 A1* | 7/2015 | Kusumoto ........... | A61B 5/4836 709/203 |
| 2016/0162728 A1 | 6/2016 | Arai et al. | |
| 2016/0357578 A1* | 12/2016 | Kim ..................... | A45D 44/005 |
| 2017/0061609 A1* | 3/2017 | Son .................... | G06Q 30/0641 |
| 2017/0319065 A1 | 11/2017 | Kimura et al. | |
| 2018/0085048 A1* | 3/2018 | Lee ....................... | G06F 3/0484 |
| 2018/0280287 A1* | 10/2018 | Gorcea ................ | A61K 8/8147 |
| 2019/0200732 A1* | 7/2019 | Shinoda ................. | A45D 44/22 |
| 2020/0066405 A1* | 2/2020 | Peyman .................. | G06N 3/08 |

\* cited by examiner

FIG. 14

NEW PATIENT REGISTRATION

SURNAME: SNOW

GIVEN NAME(S): BEAUTY

DATE OF BIRTH: 02/03/2017

HOSPITAL CARD NO.: 04321

REGISTER | SYNCHRONIZE WITH ELECTRONIC HEALTH RECORDS

FIG. 15

PATIENT SEARCH

HOSPITAL CARD NO.

SURNAME

GIVEN NAME(S)

DATE OF BIRTH: 01/01/2017

SEARCH     FROM ELECTRONIC HEALTH RECORDS

| PATIENT ATTRIBUTES | DATE OF TREATMENT | CONTENT OF TREATMENT | POSITION OF TREATMENT | NUMBER OF TIMES OF TREATMENT | SKIN SCORE |
|---|---|---|---|---|---|
| FEMALE, THIRTIES | 04/30/2018 | HYALURONIC ACID INJECTION | (2, -1) | 1 | 100 |

SKIN ANALYZING DEVICE, SKIN ANALYZING METHOD, AND RECORDING MEDIUM

BACKGROUND

1. Technical Field

The present disclosure relates to a skin analyzing device, a skin analyzing method, and a recording medium.

2. Description of the Related Art

Analyzing the facial skin condition of a measurement subject based on a facial image where the face of the subject has been photographed, and visualizing and quantifying the analysis results, has been performed conventionally. International Publication No. 2015/015793 discloses a device that automatically recognizes the position of the facial portion from a facial image, and automatically sets a region (hereinafter referred to as "skin analysis region") that is the object of analysis of the skin, based on the position of the facial portion that has been recognized.

Facial images taken at different timings may have different facial sizes and/or compositions, or the like. Japanese Unexamined Patent Application Publication No. 2010-86036 discloses a method of compositing and displaying a facial image of a subject wearing makeup taken this time, and a facial image of the subject wearing makeup taken in the past, at a predetermined ratio. Also see, for example, Japanese Unexamined Patent Application Publication No. 2003-187251.

SUMMARY

However, the length to width ratio of the facial image for comparison is changed in the method described in Japanese Unexamined Patent Application Publication No. 2010-86036, and accordingly the method cannot be applied in a case of recognizing change in skin condition focusing on a partial region of the face (hereinafter referred to as "region of interest"), such as in a case where treatment has been performed on a part of the face, for example.

One non-limiting and exemplary embodiment provides a skin analyzing device, a skin analyzing method, and a recording medium, capable of easily recognizing change in skin condition of a region of interest, even if facial images are taken at different timings.

In one general aspect, the techniques disclosed here feature a skin analyzing device, including: a facial coordinates setter that sets facial coordinates on a facial image of a measurement subject by using, as a reference, a position of a facial portion identified from the facial image; a region-of-interest setter that sets a first region of interest to a first facial image of the measurement subject, and sets a second region of interest that has facial coordinates in common with the first region of interest to a second facial image of the measurement subject; and a skin analysis user interface (UI) that displays the first facial image and the second facial image next to each other, and displays a skin analysis result in the first region of interest with respect to the first facial image, and a skin analysis result in the second region of interest with respect to the second facial image.

According to one non-limiting and exemplary embodiment of the present disclosure, change in skin condition of a region of interest can easily be recognized, even if facial images are taken at different timings.

It should be noted that general or specific embodiments may be implemented as a system, a device, a method, an integrated circuit, a computer program, a storage medium, or any selective combination of system, device, method, integrated circuit, computer program, and storage medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 14 is a diagram illustrating an example of a new patient registration UI according to Embodiment 2;

FIG. 15 is a diagram illustrating an example of a patient search UI according to Embodiment 2;

FIG. 26 is a diagram illustrating a configuration example of a cooperative database according to Embodiment 3;

DETAILED DESCRIPTION

Embodiments of the present disclosure will be described in detail below with reference to the drawings as appropriate. Note, however, that unnecessarily detailed description may be omitted. For example, there are cases where detailed description of well-known items, or redundant description of configurations that are substantially the same, will be omitted. This is to avoid the following description from becoming unnecessarily lengthy, and to facilitate understanding of those skilled in the art.

Embodiment 1

Overview of Skin Analyzing Device

Figure 1:
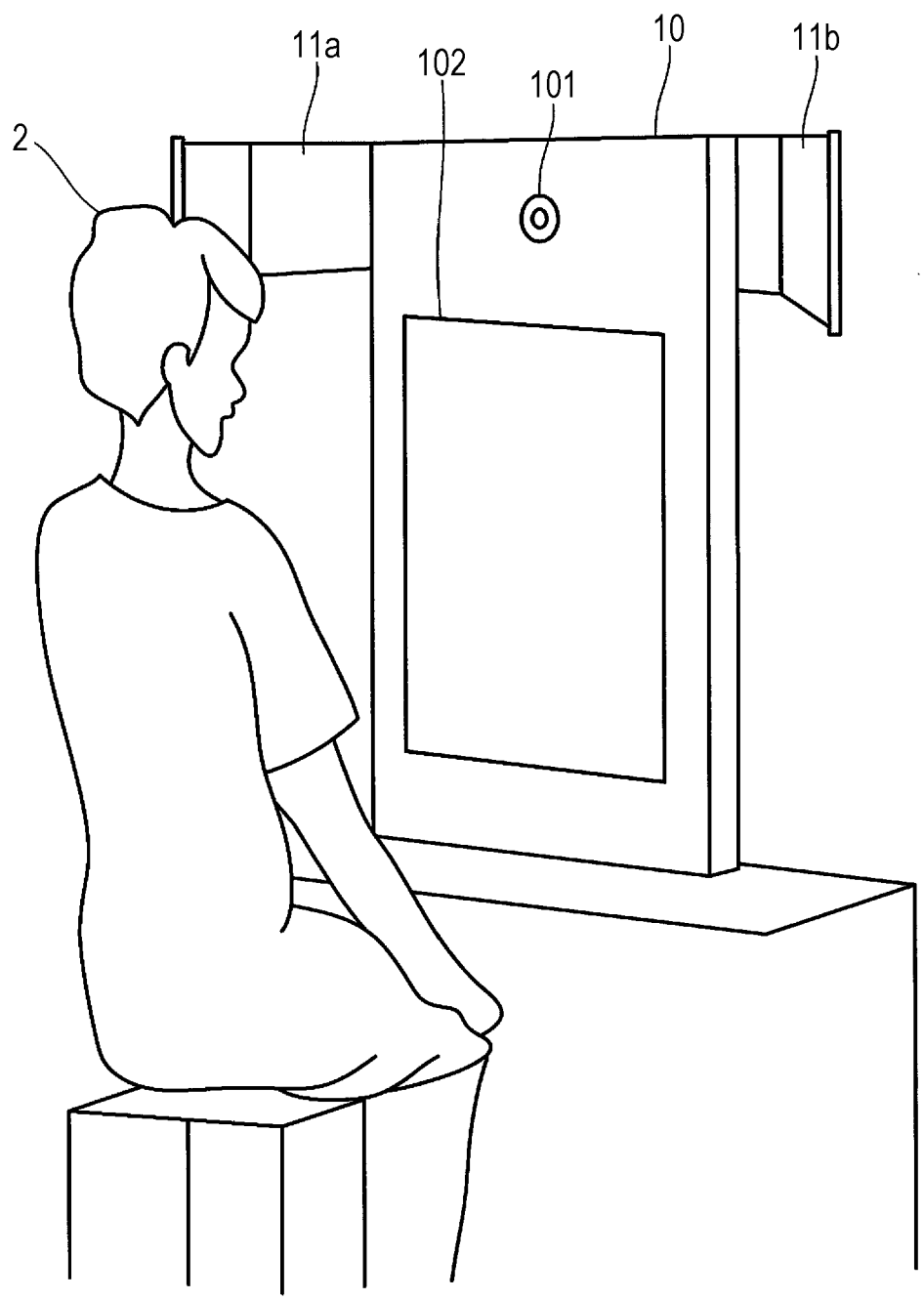
FIG. 1 is a diagram illustrating an example of using a skin analyzing device according to Embodiment 1.
Figure 2:
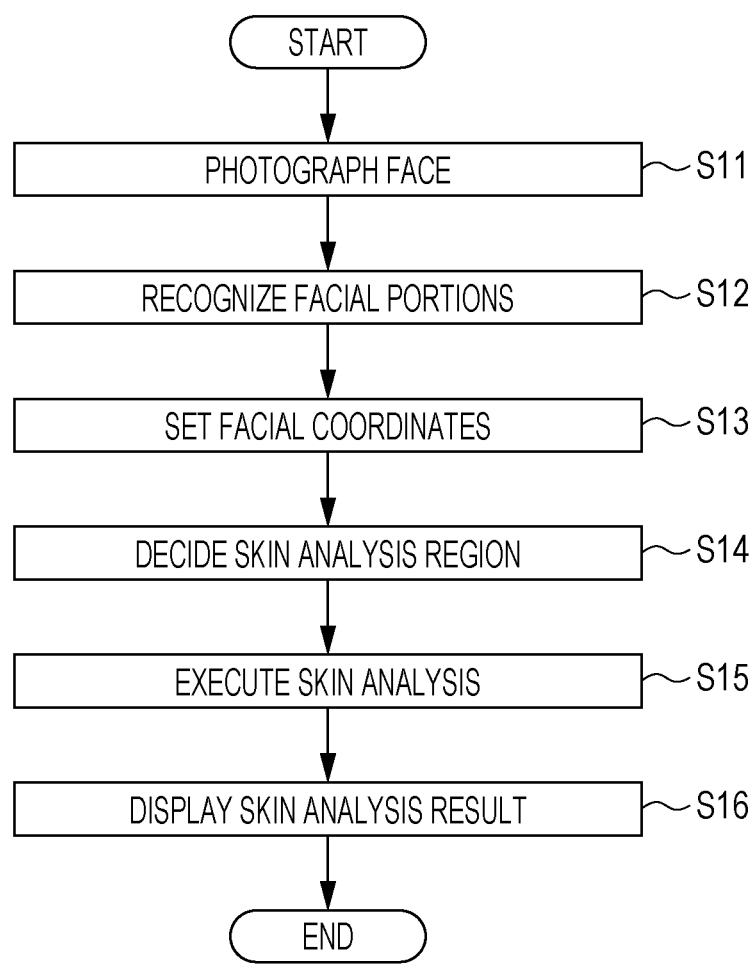
FIG. 2 is a flowchart illustrating an overview of operations of the skin analyzing device according to Embodiment 1.

FIG. 1 illustrates an example of using a skin analyzing device. The flowchart in FIG. 2 illustrates an example of an overview of operations of the skin analyzing device. An overview of the skin analyzing device will be described below with reference to FIGS. 1 and 2.

A measurement subject 2 who is to be measured for skin analysis is seated in front of a skin analyzing device 10, as illustrated in FIG. 1, and instructs the skin analyzing device 10 to start skin analysis. Upon receiving this start instruction, the skin analyzing device 10 starts the following operations.

The skin analyzing device 10 photographs the face of the measurement subject 2 using a camera 101 (S11). Hereinafter, an image, obtained by the camera 101 photographing the face of the measurement subject 2, will be referred to as a "facial image".

The skin analyzing device 10 recognizes facial portions in the facial image taken in S11 (S12). Facial portions are feature parts of the face, such as outline of the face, eyes, nose, mouth, eyebrows, hairline, and so forth, for example. Note that facial portions may also be referred to as facial parts, facial features, and so forth.

The skin analyzing device 10 sets facial coordinates on the facial image, by using, as a reference, a position of a facial portion recognized in S12 (S13). Facial coordinates will be described later.

The skin analyzing device 10 sets a region for performing skin analysis (hereinafter referred to as "skin analysis region") on the facial image, based on the position of the facial portion recognized in S12, and so forth (S14). The skin analyzing device 10 executes skin analysis with regard to the skin analysis region set in S14 (S15). The skin analyzing device 10 displays a result of the skin analysis executed in S15 on a display 102 (S16).

The measurement subject 2 can easily have skin analysis performed by using the skin analyzing device 10 as described above. This will be described in detail below.

Configuration of Skin Analyzing Device

The configuration of the skin analyzing device 10 will be described below with reference to FIG. 3.

The skin analyzing device 10 includes, for example, the camera 101, the display 102, an input interface 103, a storage unit 104, and a control unit 105. The skin analyzing device 10 may also be connected to a skin analysis database 20.

The camera 101 photographs the face of the measurement subject 2. Although FIG. 1 illustrates the camera 101 as being built into the skin analyzing device 10, the camera 101 may be a separate device from the skin analyzing device 10. In this case, the camera 101 may transmit photographed facial images to the skin analyzing device 10 via predetermined wired communication or wireless communication.

The display 102 displays images, information, and so forth. The display 102 may be a mirror display that has one-way mirror functions. Although FIG. 1 illustrates the display 102 as having been built into the skin analyzing device 10, the display 102 may be a separate device from the skin analyzing device 10. In this case, the skin analyzing device 10 may transmit data for display to the display 102 via predetermined wired communication or wireless communication.

The input interface 103 accepts instructions from a person operating the skin analyzing device 10 (hereinafter referred to as "operator"). The operator may be the same person as the measurement subject, or may be a different person than the measurement subject. The skin analyzing device 10 may have multiple input interfaces 103. For example, the skin analyzing device 10 may have a touchscreen, mouse, keyboard, photography instruction button, microphone for audio input, and so forth, as input interfaces 103. The input interface 103 may be a separate device from the skin analyzing device 10. In this case, the input interface 103 may transmit input data to the skin analyzing device 10 via predetermined wired communication or wireless communication.

The storage unit 104 is a device for storing data used by the control unit 105. The storage unit 104 may be volatile memory such as dynamic random access memory (DRAM), or may be non-volatile memory such as a solid state drive (SSD), or may be a combination thereof.

The control unit 105 is a device for realizing functions that the skin analyzing device 10 has, and is, for example, a central processing unit (CPU). The control unit 105 may, by executing a computer program stored in the storage unit 104, realize functions relating to a photography processing unit 201, a facial portion recognizing unit 202, a facial coordinates setting unit 203, an analysis region setting unit 204, a skin analysis executing unit 205, a skin analysis user interface (UI) unit 206, and a region-of-interest setting unit 207, which will be described later, for example.

The photography processing unit 201 photographs the face of the measurement subject 2 by controlling the camera 101, and generates a facial image. Note that the photography processing unit 201 may display a facial image being photographed by the camera 101 on the display 102 in real time. Thus, the operator can adjust the position, direction, and so forth, of the face, while viewing the display 102, so that the face of the measurement subject 2 is correctly photographed.

The photography processing unit 201 may photograph the front of the face, the left side of the face, and the right side of the face, of the measurement subject 2. The skin analyzing device 10 may be provided with a mirror 11a that is situated at a position to the left side of the camera 101 as viewed from the measurement subject 2, and a mirror 11b that is situated at a position to the right side of the camera 101 as viewed from the measurement subject 2, as illustrated in FIG. 1, so that the left side of the face and the right side of the face will be properly photographed. The orientation (angle) of the mirror 11a at the left side may be such that the camera 101 can take an appropriate right-side face of the measurement subject 2 when the front of the face of the measurement subject 2 is facing the mirror 11a at the left side. The orientation (angle) of the mirror 11b at the right side may be such that the camera 101 can take an appropriate left-side face of the measurement subject 2 when the front of the face of the measurement subject 2 is facing the mirror 11b at the right side.

Figure 4:
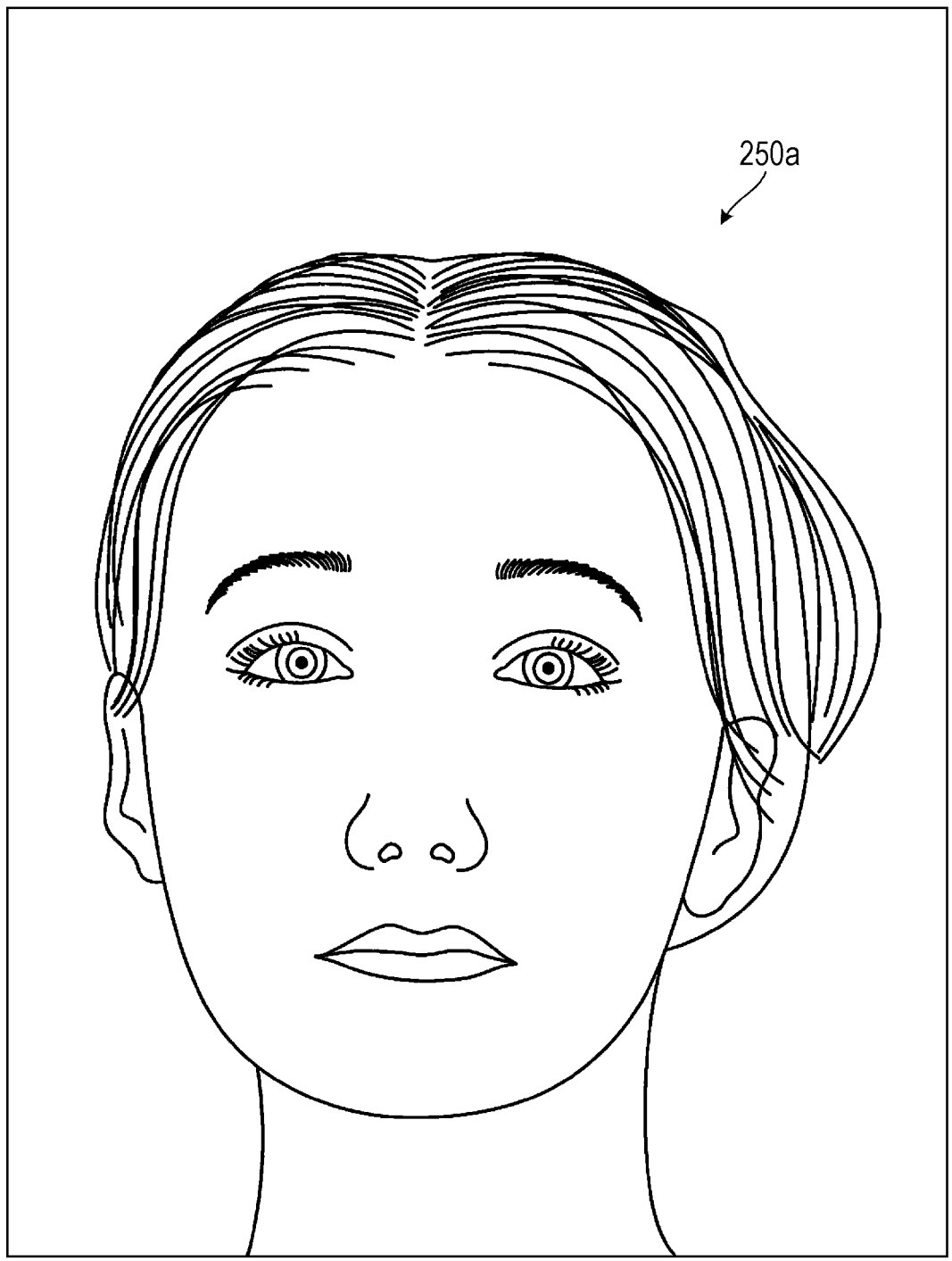
FIG. 4 is a diagram illustrating an example of a facial image of the front of the face, taken by the skin analyzing device according to Embodiment 1.
Figure 5:
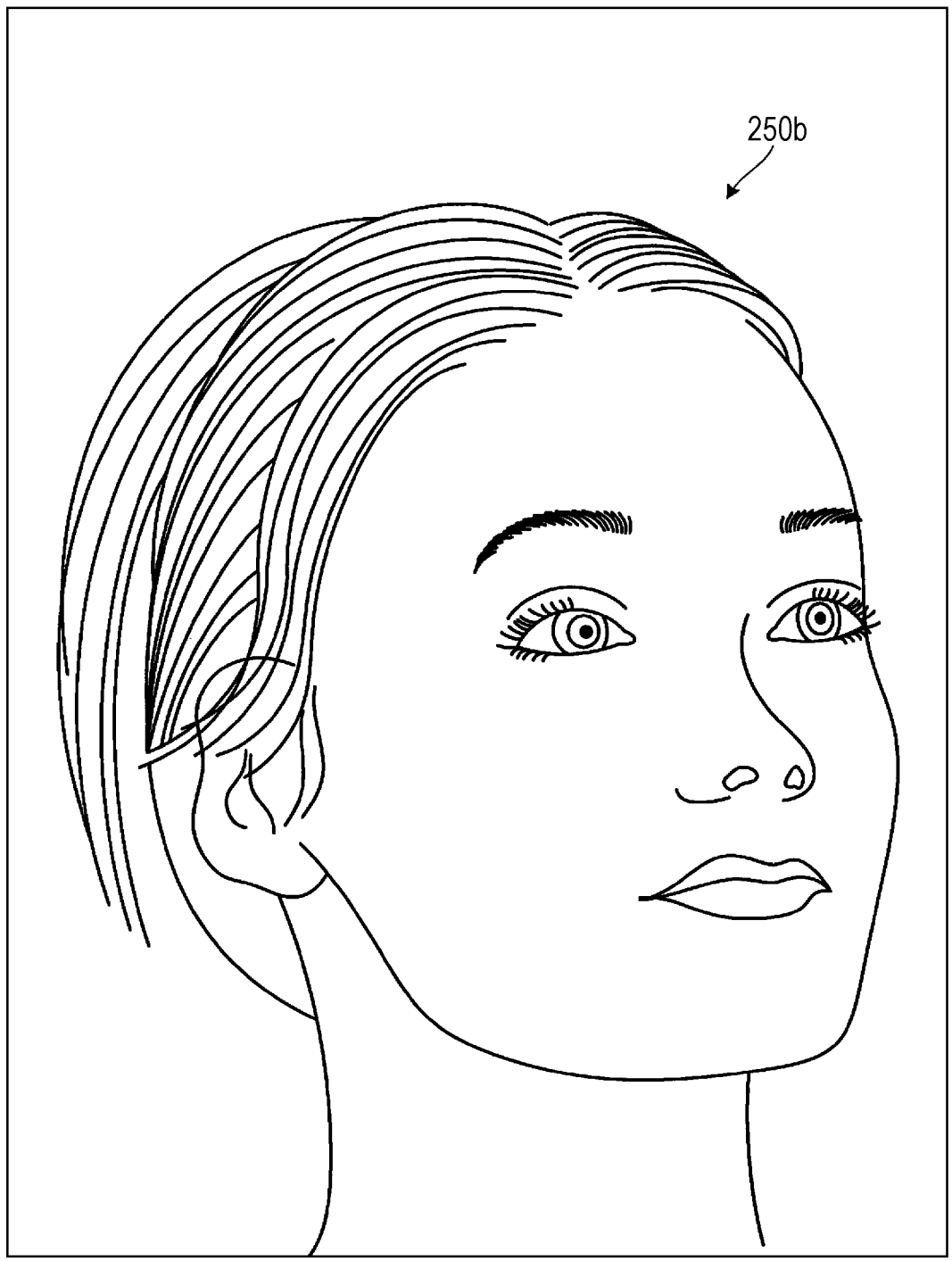
FIG. 5 is a diagram illustrating an example of a facial image of the right side of the face, taken by the skin analyzing device according to Embodiment 1.
Figure 6:
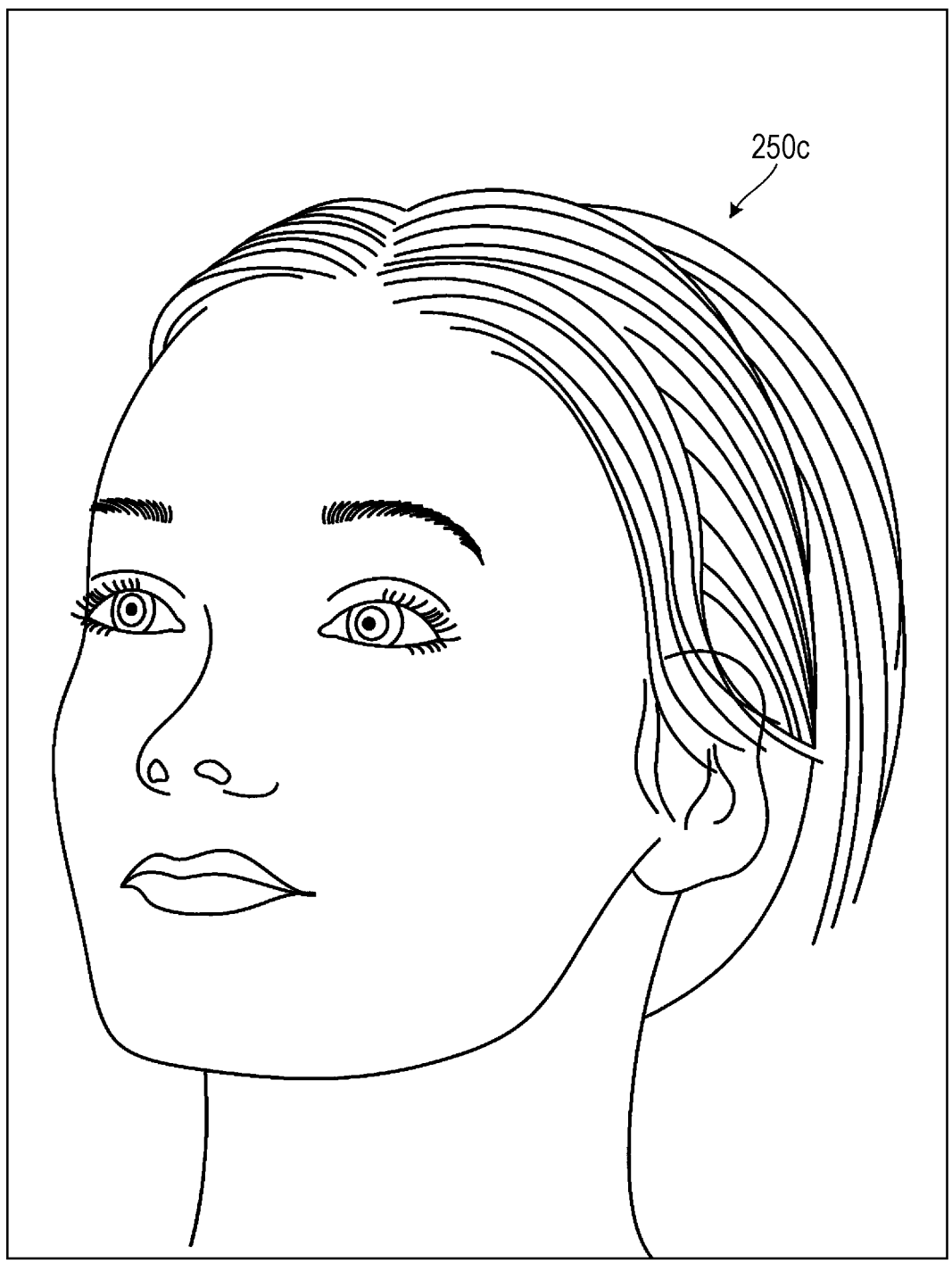
FIG. 6 is a diagram illustrating an example of a facial image of the left side of the face, taken by the skin analyzing device according to Embodiment 1.

The photography processing unit 201 may instruct the measurement subject 2 to face the front when photographing, and photograph the front of the face from the camera 101. FIG. 4 is an example of a facial image 250a of the front of the face of the measurement subject 2 having been photographed. The photography processing unit 201 may next instruct the measurement subject 2 to change the direction of the face so that the front of the face faces the mirror 11a at the left side so as to be reflected therein, and photograph the right side of the face from the camera 101. FIG. 5 is an example of a facial image 250b of the right side of the face of the measurement subject 2 having been photographed. The photography processing unit 201 may finally instruct the measurement subject 2 to change the direction of the face so that the front of the face faces the mirror 11b at the right side so as to be reflected therein, and photograph the left side of the face from the camera 101. FIG. 6 is an example of a facial image 250c of the left side of the face of the measurement subject 2 having been photographed. Hereinafter, the front of the face, the left side of the face, and the right side of the face will be referred to simply as "facial image" if there is no need to distinguish therebetween.

The facial portion recognizing unit 202 recognizes facial portions by the following processing, for example. First, the facial portion recognizing unit 202 uses known image processing technology to extract feature points from a facial image 250. Next, the facial portion recognizing unit 202 recognizes facial portions, such as the outline of the face, eyes, nose, mouth, eyebrows, hairline, and so forth, from the extracted feature points.

The facial coordinates setting unit 203 sets, by using a position of a facial portion (e.g., both eyes) recognized by the facial portion recognizing unit 202 as a reference, relative coordinates (hereinafter referred to as "facial coordinates") to the facial image, with the position of the facial portion identified from the facial image as a reference. Facial coordinates are set for each facial image. Note that details of the facial coordinates setting unit 203 will be described later in "Details of Facial Coordinates Setting Unit".

The analysis region setting unit 204 sets at least one skin analysis region in the facial image, based on positions of the facial portions recognized by the facial portion recognizing unit 202 and so forth.

The skin analysis executing unit 205 executes skin analysis with regard to each skin analysis region set in the facial image by the analysis region setting unit 204. For example, the skin analysis executing unit 205 applies known image processing to the skin analysis region of the facial image to analyze the amount of wrinkles, blemishes, and/or pores and so forth. The skin analysis executing unit 205 stores the facial image, the facial coordinates set on the facial image, and the skin analysis results of the facial image, in the skin analysis database 20, in a correlated manner.

The skin analysis UI unit 206 generates a UI and displays it on the display 102, and accepts operations performed as to the UI via the input interface 103. For example, the skin analysis UI unit 206 displays images and information relating to results of processing by the components 201 through 207 on the display 102. The skin analysis UI unit 206 transmits content of operations performed by the measurement subject 2, input via the input interface 103, to the components 201 through 207.

The skin analysis UI unit 206 generates and displays a comparative UI that includes first and second facial images of the same measurement subject selected from the skin analysis database 20, and skin analysis result of each of the first and second facial images. Note that details of the skin analysis UI unit 206 will be described later in "Details of Comparative UI".

The region-of-interest setting unit 207 sets a first region of interest as to the first facial image, and sets a second region of interest that has facial coordinates in common with the first region of interest as to the second facial image. Accordingly, the first region of interest and the second region of interest are set to a common position on the actual face of the measurement subject, even in a case where the scale or composition of the face of the measurement subject photographed in the first facial image and second facial image differ. Note that details of the region-of-interest setting unit 207 will be described later in "Details of Comparative UI".

The skin analysis database 20 manages facial images of the measurement subject 2, facial coordinates set as to the facial images, and skin analysis results of the facial images, in a correlated manner. While the skin analysis database 20 is illustrated as being a separate device from the skin analyzing device 10 in FIG. 3, the skin analysis database 20 may be built into the skin analyzing device 10.

Details of Facial Coordinates Setting Unit

Even facial images of the same measurement subject differ with regard to the size of the face in the facial images, and so forth, if taken at different timings (e.g., at different times of day or on different days). Also, even facial images of the same measurement subject differ with regard to composition of the face in the facial images if taken at different angles. On the other hand, even though sizes and compositions differ in facial images of the same measurement subject, the positional relation of facial portions hardly changes at all. Accordingly, the facial coordinates setting unit 203 sets, with a facial portion identified from the facial image as a reference, relative coordinates (facial coordinates) 400, as to the facial image. Accordingly, a position on the actual face of the measurement subject can be specified using the facial coordinates 400, even in a case where facial images of the same measurement subject differ with regard to size or composition or the like.

Figure 7:
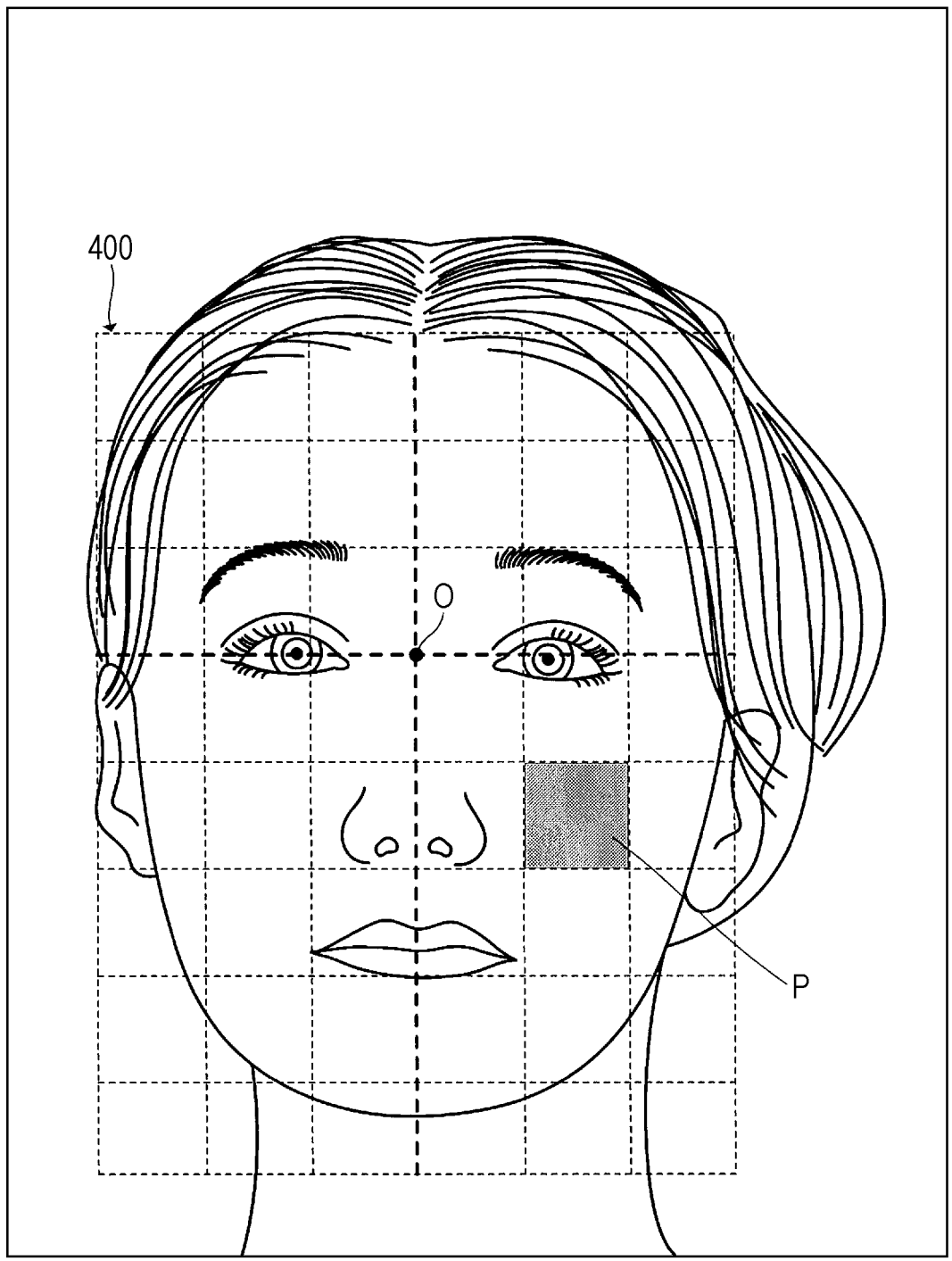
FIG. 7 is a diagram illustrating an example of facial coordinates set on the facial image of the front of the face, according to Embodiment 1.
Figure 8:
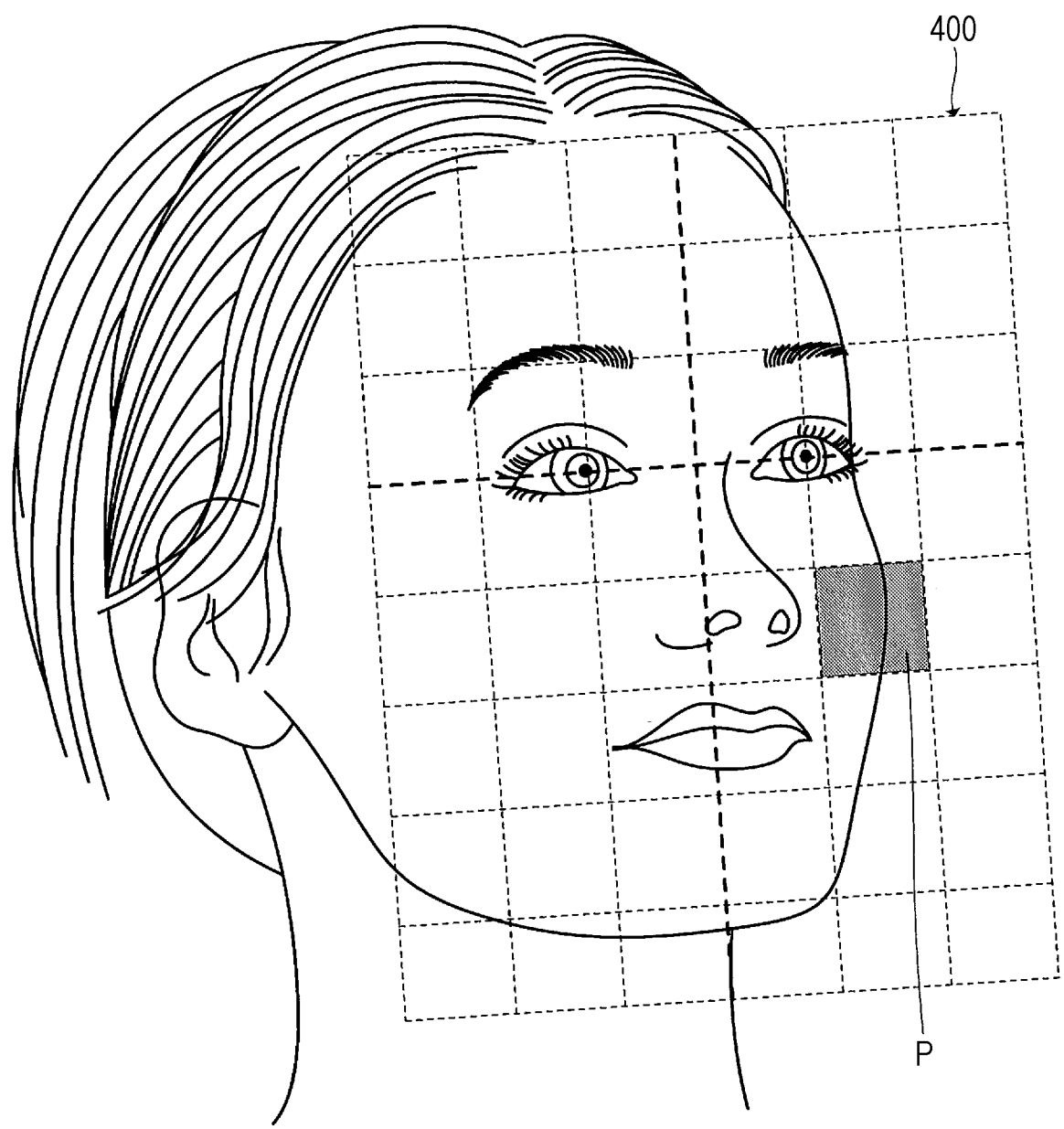
FIG. 8 is a diagram illustrating an example of facial coordinates set on the facial image of the right side of the face, according to Embodiment 1.
Figure 9:
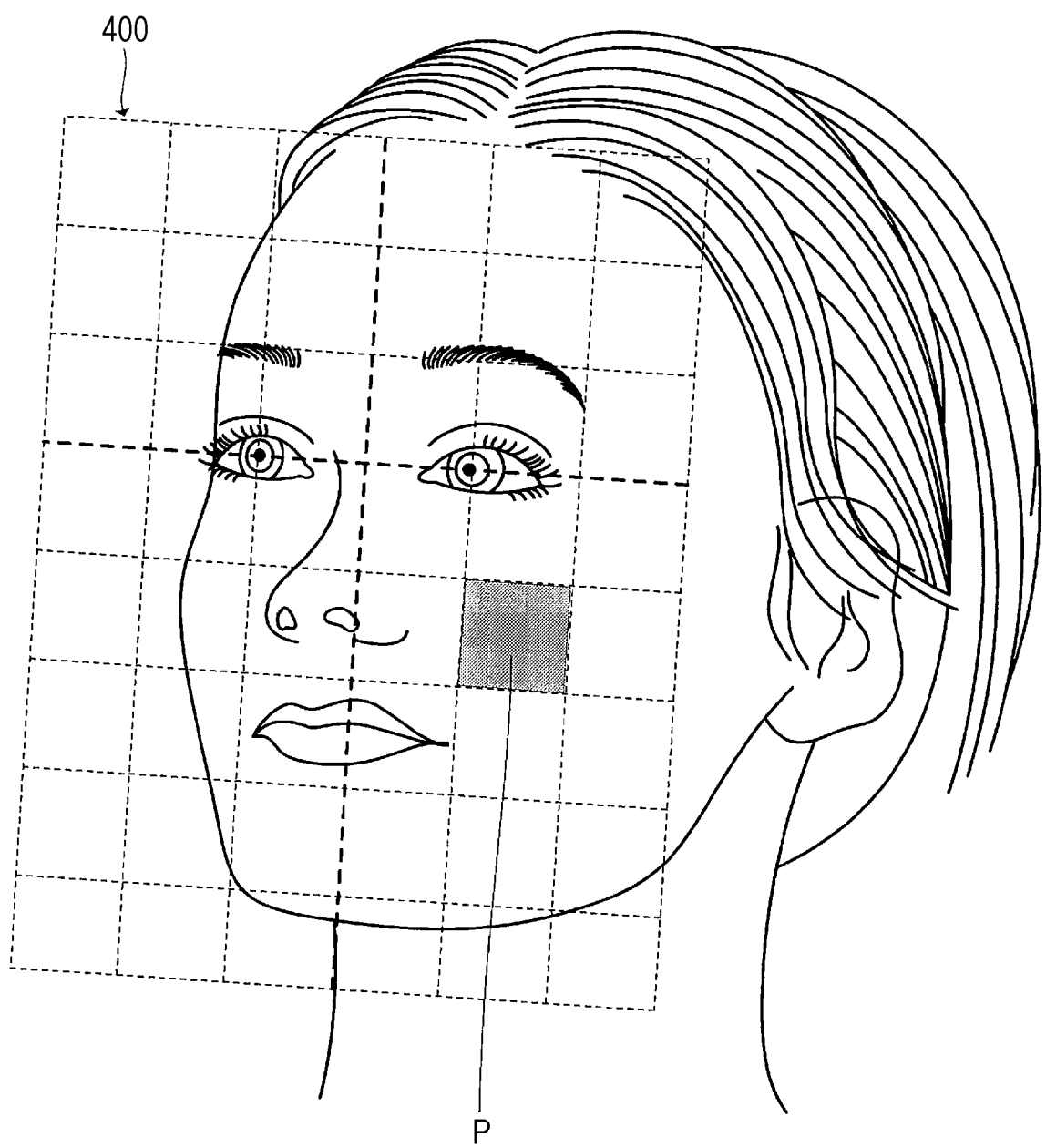
FIG. 9 is a diagram illustrating an example of facial coordinates set on the facial image of the left side of the face, according to Embodiment 1.
Figure 10:
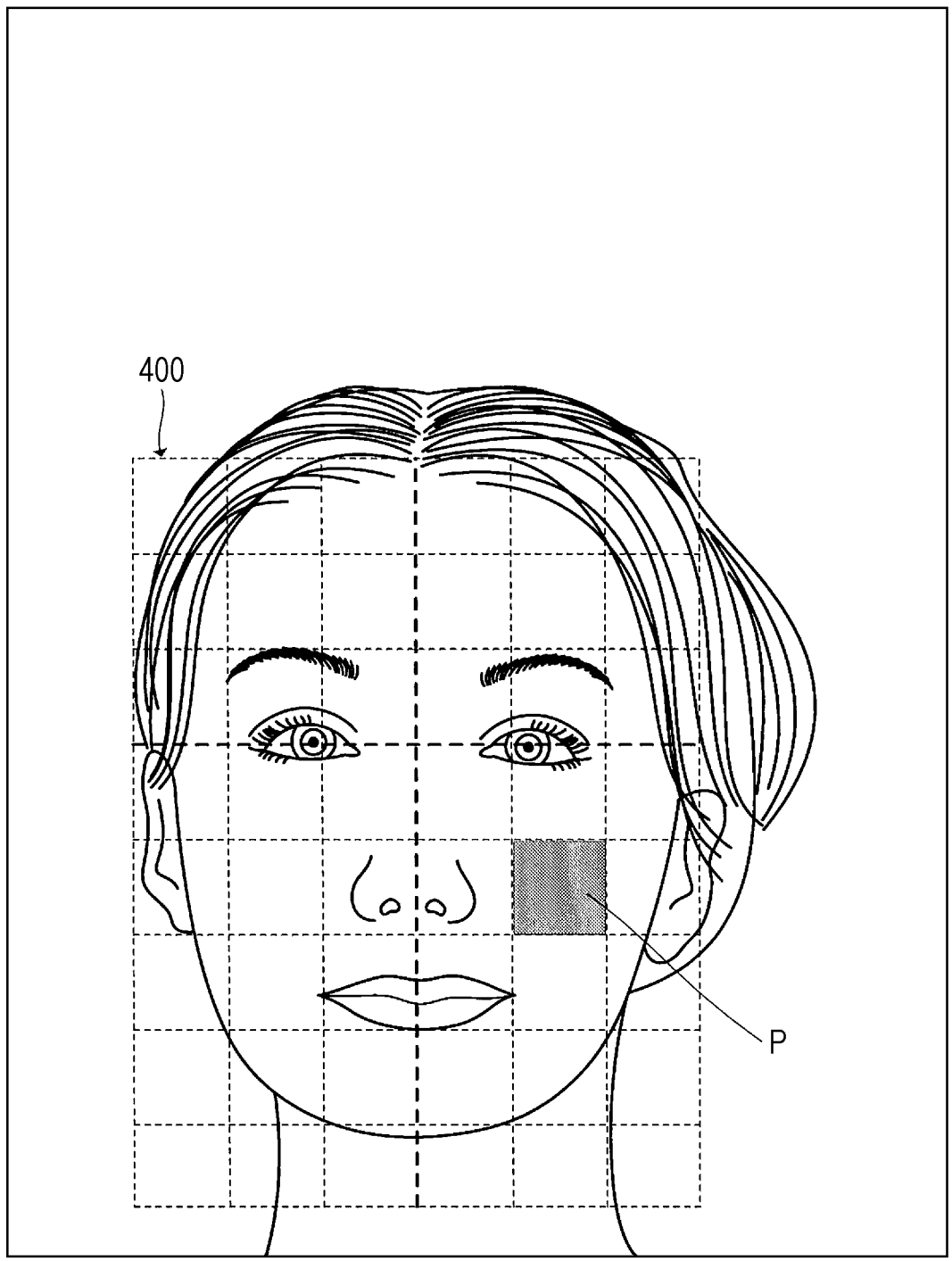
FIG. 10 is a diagram illustrating an example of facial coordinates set on a facial image, different in scale, of the front of the face, according to Embodiment 1.

Next, an example of facial coordinates will be described with reference to FIGS. 7 through 10. FIG. 7 is a diagram illustrating an example of facial coordinates 400 set on the facial image of the front of the face. FIG. 8 is a diagram illustrating an example of facial coordinates 400 set on the facial image of the right side of the face. FIG. 9 is a diagram illustrating an example of facial coordinates 400 set on the facial image of the left side of the face. FIG. 10 is a diagram illustrating an example of facial coordinates 400 set on a facial image of the front of the face that is of a different size as the face in the facial image in FIG. 7.

For example, the facial coordinates setting unit 203 may set facial coordinates 400 where the center of a straight line connecting the right and left eyes in a facial image is the origin O, as illustrated in FIG. 7. The facial coordinates setting unit 203 may decide a unit length of the facial coordinates 400 (length of one side of one section illustrated in FIG. 7) in accordance with the length from the origin O to the center of an eye. For example, the facial coordinates setting unit 203 may decide the length from the origin O to the center of the left eye (or right eye) to be the unit length of the facial coordinates 400. Also, in a case where the straight line connecting the left and right eyes in the facial image is inclined, the facial coordinates setting unit 203 may set facial coordinates 400 matching that incline, as illustrated in FIGS. 8 and 9, for example.

Accordingly, a common position on the actual face of the measurement subject can be specified by specifying a region (hereinafter referred to as "facial coordinates region") P defined by common facial coordinates 400 with regard to facial images with different angles and/or facial images with different face sizes, as illustrated in FIGS. 7 through 10.

Details of Skin Analysis UI Unit

Figure 11:
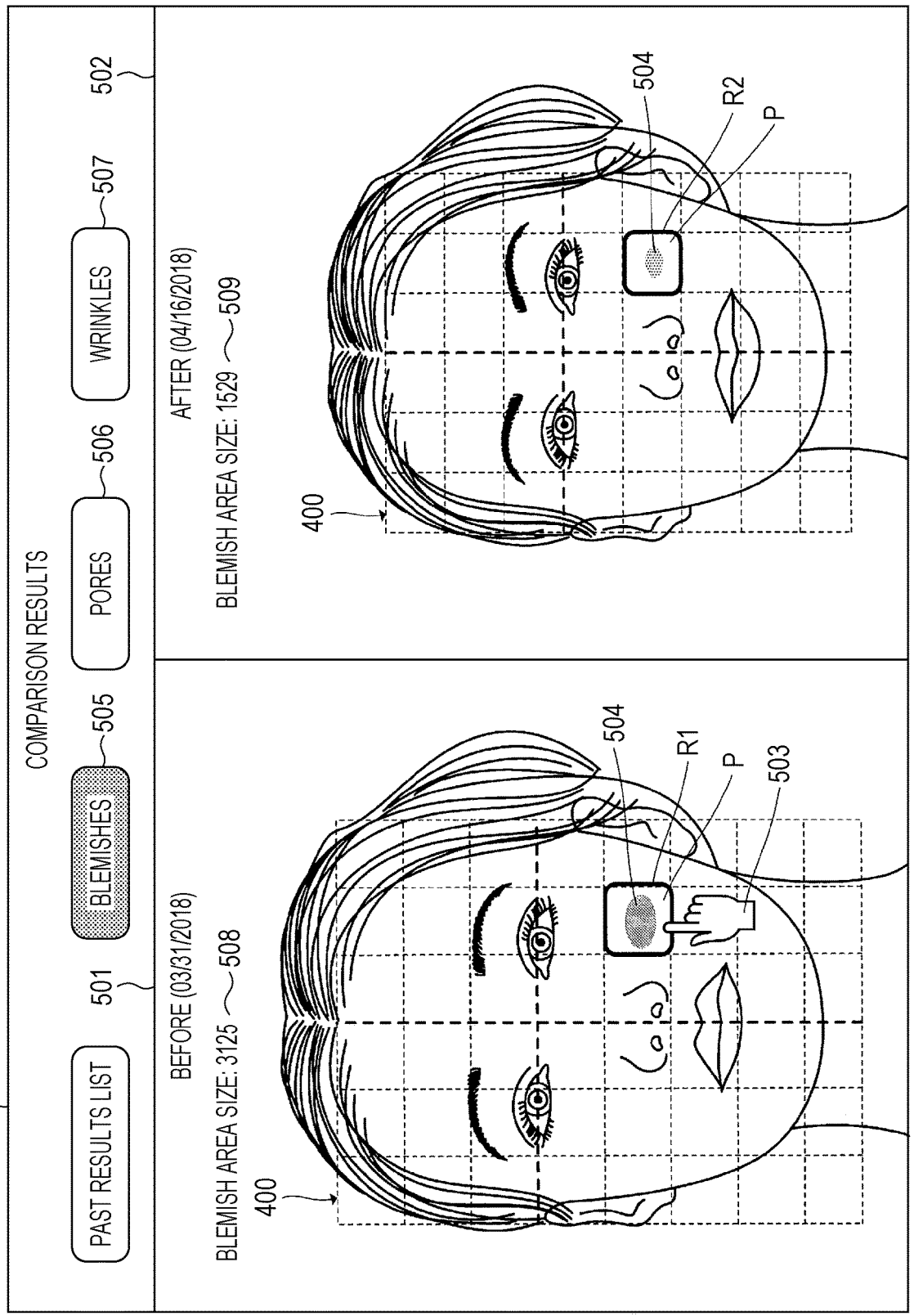
FIG. 11 is a diagram illustrating an example of a comparative user interface (UI) according to Embodiment 1.

FIG. 11 illustrates an example of a comparative UI that the skin analysis UI unit 206 generates.

The skin analysis UI unit 206 generates and displays a comparative UI 500 where first skin analysis result 501 and second skin analysis result 502 of the same measurement subject are arrayed, as exemplified in FIG. 11. Note that the facial coordinates 400 are also shown in FIG. 11 to facilitate description, but the facial coordinates 400 may be hidden from display in the comparative UI 500.

In a case where the operator operates a finger icon 503 for example, and sets a region of interest R1 on the facial image in the first skin analysis result 501 as illustrated in FIG. 11, the region-of-interest setting unit 207 performs the following processing. That is to say, the region-of-interest setting unit 207 calculates a facial coordinates region P corresponding to the region of interest R1 from the facial coordinates 400 set on the facial image in the first skin analysis result 501, and sets a region of interest R2 in the facial coordinates region P that has been calculated, on the facial coordinates 400 set to the facial image in the second skin analysis result 502.

On the other hand, in a case where the operator sets a region of interest R2 on the facial image in the second skin analysis result 502, the region-of-interest setting unit 207 performs the following processing. That is to say, the region-of-interest setting unit 207 calculates a facial coordinates region P corresponding to the region of interest R2 from the facial coordinates 400 set on the facial image in the second skin analysis result 502, and sets a region of interest R1 in the facial coordinates region P that has been calculated, on the facial coordinates 400 set to the facial image in the first skin analysis result 501.

Note that the skin analysis UI unit 206 may display a frame indicating the region of interest R1 on the facial image in the first skin analysis result 501, and may display a frame indicating the region of interest R2 on the facial image in the second skin analysis result 502.

The size of the regions of interest R1 and R2 may be input by the operator. Alternatively, the size of the regions of interest R1 and R2 may be set beforehand for each skin analysis object 504 (e.g., blemish, wrinkle, pore, etc.). Note that while the size of a region of interest is one section of the facial coordinates 400 in FIG. 11, the size of the region of interest may be two or more sections, or may be smaller than one section.

Also, the skin analysis objects 504 in the comparative UI 500 may be switchable by a "blemish" button 505, a "pores" button 506, and a "wrinkles" button 507 illustrated in FIG. 11. For example, when the "blemish" button 505 is pressed, skin analysis results regarding blemishes within the regions of interest R1 and R2 may be displayed.

Also, the skin analysis UI unit 206 may display skin analysis objects 504 recognized in regions of interest R1 and R2, in a form distinguishable from the color of skin in the comparative UI 500. For example, the skin analysis UI unit 206 may display skin analysis objects 504 according to the following A1, A2, A3, or a combination thereof.

A1: The skin analysis UI unit 206 displays portions with blemishes, pores, or wrinkles, in the regions of interest R1 and R2, using a hue that greatly differs from the color of skin (highlight display). Note that the skin analysis UI unit 206 may display only the outlines of portions with blemishes, pores, or wrinkles highlighted. The skin analysis UI unit 206 may make enlarged display of the regions of interest R1 and R2.

A2: The skin analysis UI unit 206 performs display where the darkness of the color of highlight display is differentiated in accordance with the darkness of blemishes, depth of wrinkles, or size of pores, in the regions of interest R1 and R2.

A3: The skin analysis UI unit 206 displays a skin score 508 in the region of interest R1, and a skin score 509 in the region of interest R2. A skin score is a value calculated in accordance with skin analysis objects 504, such as number of pores, density of pores, area size of blemishes, darkness of blemishes, area size of wrinkles, depth of wrinkles, and so forth, for example.

According to the comparative UI 500, difference or change in skin analysis objects 504 at a desired position on the face of the measurement subject can be recognized visually (e.g., highlight display) and/or numerically (e.g., skin score). For example, in a case of the measurement subject receiving treatment for part of the face, change of the skin analysis object 504 at the treated position before and after treatment can easily be recognized by displaying skin analysis result before treatment and skin analysis result after treatment on the comparative UI 500, and setting the position of the treatment to a region of interest.

Embodiment 2

Using the skin analyzing device 10 enables the effects of treatment on a patient (measurement subject) that has received treatment at a part of the face to be measured. Also, many medical facilities nowadays manage content of treatment using electronic health records. Accordingly, a skin analyzing device 10 that can cooperate with electronic health records will be described in Embodiment 2.

Figure 12:
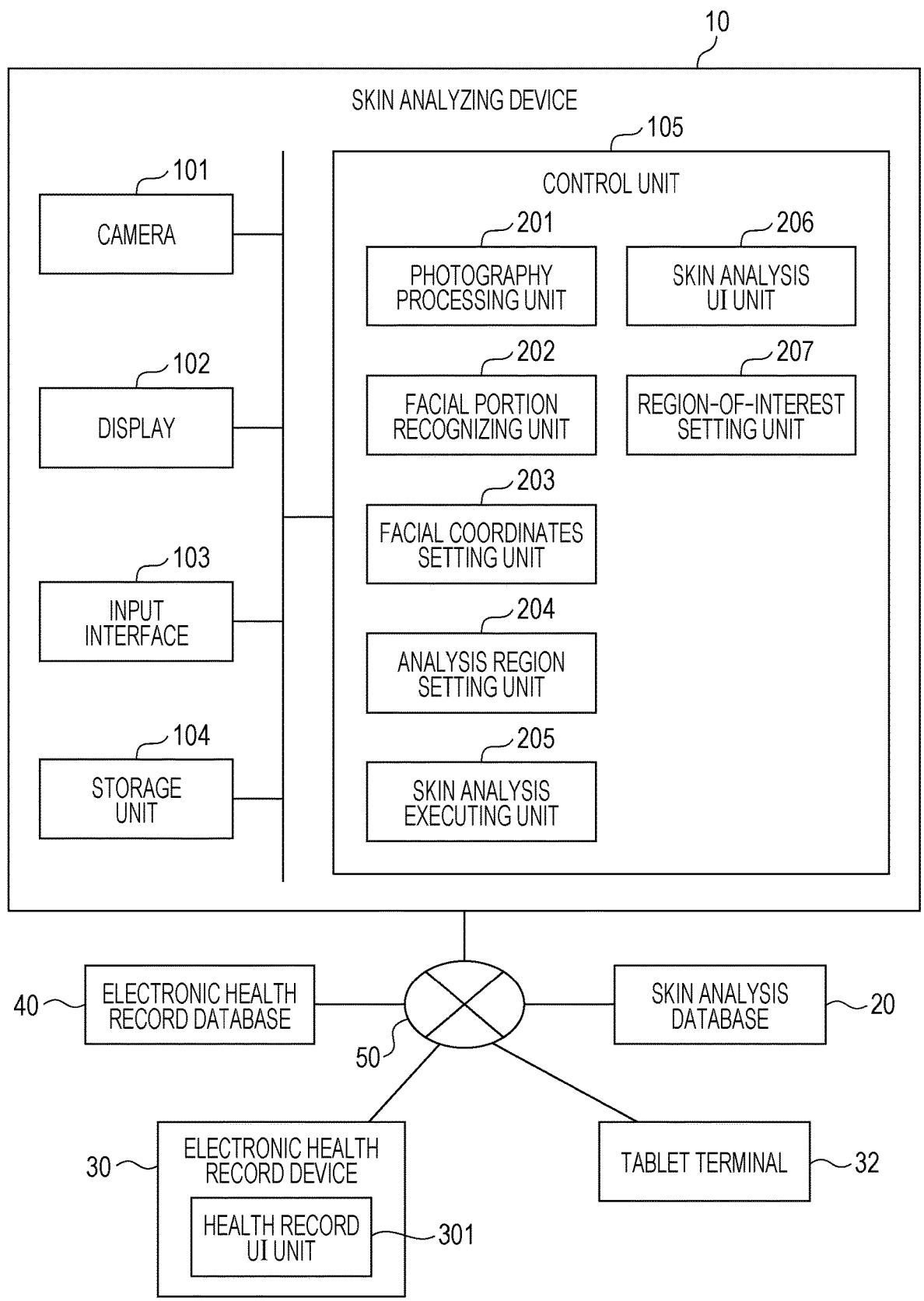
FIG. 12 is a diagram illustrating a configuration example of a cooperative system according to Embodiment 2.

FIG. 12 illustrates a configuration example of a cooperative system according to Embodiment 2.

The cooperative system has, for example, the skin analyzing device 10, the skin analysis database 20, an electronic health record device 30, a tablet terminal 32, and an electronic health record database 40. These devices 10, 20, 30, 32, and 40 are capable of exchanging data via a communication network 50 (e.g., a local area network (LAN), the Internet, etc.). Components that are the same as those in FIG. 3 may be denoted by the same reference numerals and description thereof be omitted.

The electronic health record device 30 is a personal computer (PC), for example, that provides electronic health record functions to a medical worker such as a physician, nurse, or the like. The electronic health record device 30 includes a health record UI unit 301, for example. The health record UI unit 301 provides medical workers with a health record UI that is a UI for using electronic health records, and accepts input to electronic health records and so forth. The health record UI unit 301 stores content input at the health record UI in the electronic health record database 40.

The tablet terminal 32 is a portable device that has a touchscreen display, for example. The tablet terminal 32 is used in cooperation with the skin analyzing device 10 and/or electronic health record device 30.

Flow of Examination

Next, an example of the flow of an examination will be described with reference to the flowchart in FIG. 13.

First, a medical worker (operator) uses the skin analyzing device 10 to take facial images of a patient (measurement subject). The skin analyzing device 10 performs skin analysis on the facial images that have been photographed, and records the skin analysis result in the skin analysis database 20 (S51).

Next, the physician operates the health record UI to search for electronic health records of the patient from the electronic health record database 40, in order to perform an examination of the patient (S52).

The physician then confirms the content of treatment (e.g., date and body part where treatment was performed last or the like) from the electronic health records of the patient (S53). At this time, the electronic health record device 30 transmits the hospital card No. of the patient being displayed, body portion treated, and/or date for comparison, and so forth, to the tablet terminal 32 as search keys, and the tablet terminal 32 obtains a skin analysis result corresponding to the search keys from the skin analysis database 20 and performs display thereof (S54). Accordingly, the physician can display the skin analysis result of the patient on the tablet terminal 32, which can be shown to the patient. That is to say, smooth counseling of the patient is facilitated for the physician.

Finally, the physician records the content of treatment of that day, and the result of the counselling such as the content planned for the next treatment, in the electronic health records (S55). The electronic health record device 30 reflects the content recorded in the electronic health records in the electronic health record database 40.

Thus, the physician may perform counselling before and after treatment, using the skin analyzing device. Note that the hospital card No. is an example of information for uniquely identifying the patient (patient ID). Accordingly, a telephone No. or the like may be used instead of the hospital card No.

Cooperation of Skin Analyzing Device, Electronic Health Record Device, and Tablet Terminal Next, an example of cooperation among the skin analyzing device 10, electronic health record device 30, and tablet terminal 32 will be described.

FIG. 14 is a diagram illustrating an example of a new patient registration UI 550. The new patient registration UI 550 is a UI for registering patient information of a patient regarding which skin analysis is to be performed for the first time. For example, the medical worker displays the new patient registration UI 550 on the skin analyzing device 10 and/or tablet terminal 32 in S51 in FIG. 13, and registers patient information.

The new patient registration UI 550 accepts input of patient information, as illustrated in FIG. 14. Patient information includes, for example, surname and given name(s) of the patient, date of birth, hospital card No., and so forth. The skin analyzing device 10 or tablet terminal 32 registers the patient information input to the new patient registration UI 550 in the skin analysis database 20.

The new patient registration UI 550 has a "synchronize with electronic health records" button 551, as illustrated in FIG. 14. When the "synchronize with electronic health records" button 551 is touched, the skin analyzing device 10 or tablet terminal 32 registers the patient information input at the new patient registration UI 550 in the electronic health record database 40 as well. Accordingly, patient information can be registered in both the skin analysis database 20 and the electronic health record database 40 with the same input.

FIG. 15 is a diagram illustrating an example of a patient search UI 560. The patient search UI 560 is a UI for searching for patient information of a patient, to perform skin analysis. For example, a medical worker displays the patient search UI 560 on the skin analyzing device 10 and/or tablet terminal 32 in S51 in FIG. 13, and searches for patient information.

The patient search UI 560 accepts input of search keys, as illustrated in FIG. 15. Search keys include, for example, surname and given name(s) of the patient, date of birth, hospital card No., and so forth. The skin analyzing device 10 or tablet terminal 32 obtains patient information corresponding to the input search keys, from the skin analysis database 20.

The patient search UI 560 has a "from electronic health records" button 561, as illustrated in FIG. 15. Upon the "from electronic health records" button 561 being touched, the skin analyzing device 10 or tablet terminal 32 uses hospital card No. or the like of the electronic health records currently displayed on the health record UI unit 301 of the electronic health record device 30, for example, as a search key to obtain patient information corresponding to that search key from the skin analysis database 20. Accordingly, patient information of the patient to be examined can be obtained without having to input a search key such as the hospital card No. or the like.

Figure 16:
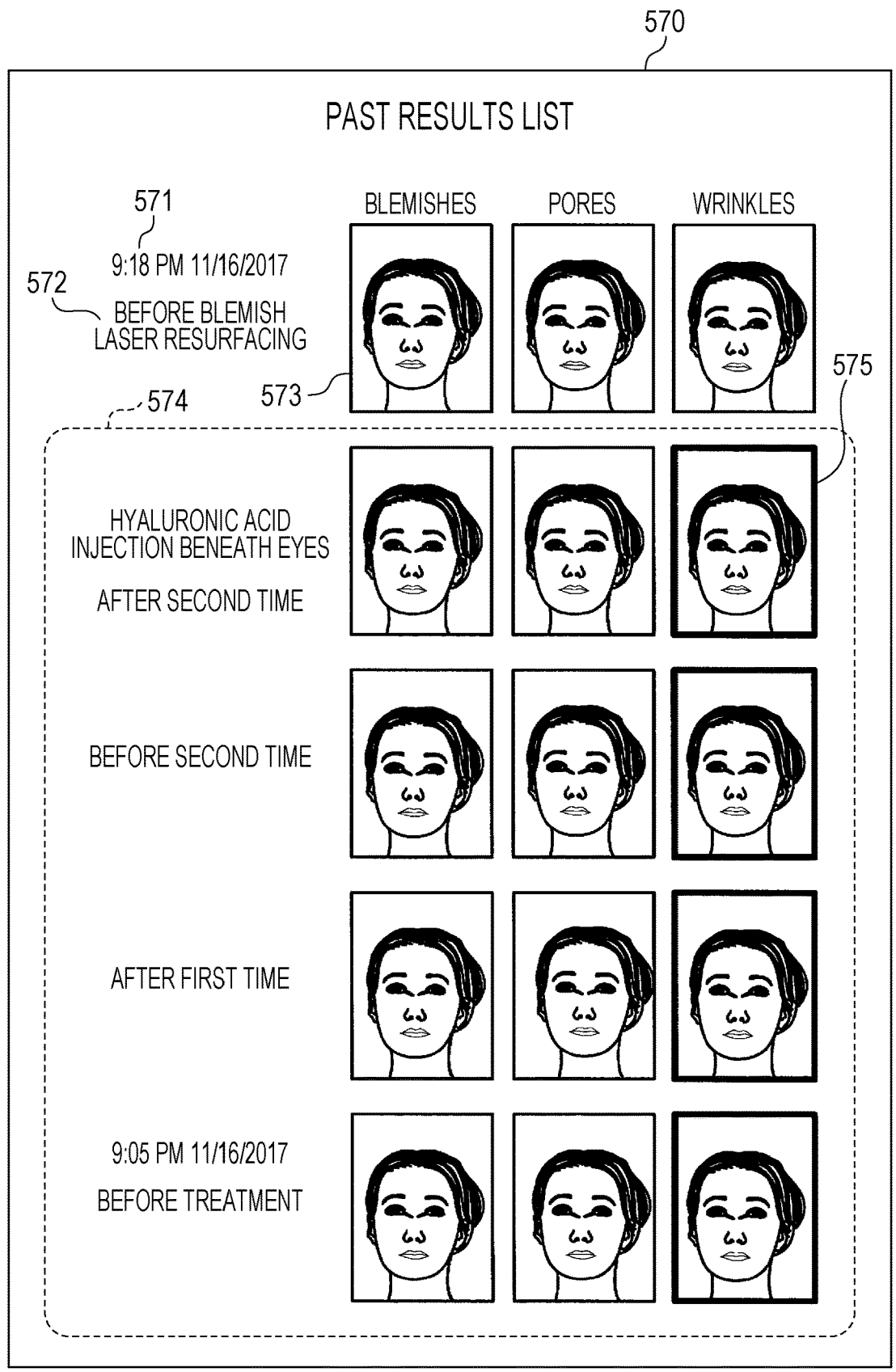
FIG. 16 is a diagram illustrating an example of a past results list UI according to Embodiment 2.

FIG. 16 is a diagram illustrating an example of a past results list UI 570. The past results list UI 570 is a UI for displaying a list of past skin analysis results of the patient. For example, a medical worker displays the past results list UI 570 on the skin analyzing device 10 and/or tablet terminal 32 in S51 in FIG. 13, and confirms past skin analysis results of the patient.

The past results list UI 570 correlates and displays, as a skin analysis result, a date and time 571 of having performed skin analysis, treatment information 572 relating to that date and time, and facial images 573 indicating the result of the skin analysis, as illustrated in FIG. 16. The skin analyzing device 10 or tablet terminal 32 may obtain the treatment information 572 relating to the date and time from the electronic health record database 40, using the patient information and date and time as search keys. The treatment information 572 may include the content of treatment (laser resurfacing for blemishes, hyaluronic acid injection beneath the eyes, etc.), and the number of times treatment was performed (once, twice, etc.), for example.

The past results list UI 570 may display facial images indicating analysis results for analysis objects (e.g., blemishes, pores, and wrinkles), as the facial images 573 indicating the results of skin analysis.

The past results list UI 570 may also display a group of the analysis results, with treatment content in common classified into one group 574. The skin analysis results may be displayed in array in order of date when skin analysis was performed within the group 574.

The past results list UI 570 may perform highlighted display of facial images corresponding to a selected analysis object (indicated by heavy line frames 575 of facial images in FIG. 16). FIG. 16 illustrates an example where the treatment content of "hyaluronic acid injection beneath the eyes" is grouped into one group 574, and within this group 574, facial images for the analysis object "wrinkles" are displayed highlighted (575).

Figure 13:
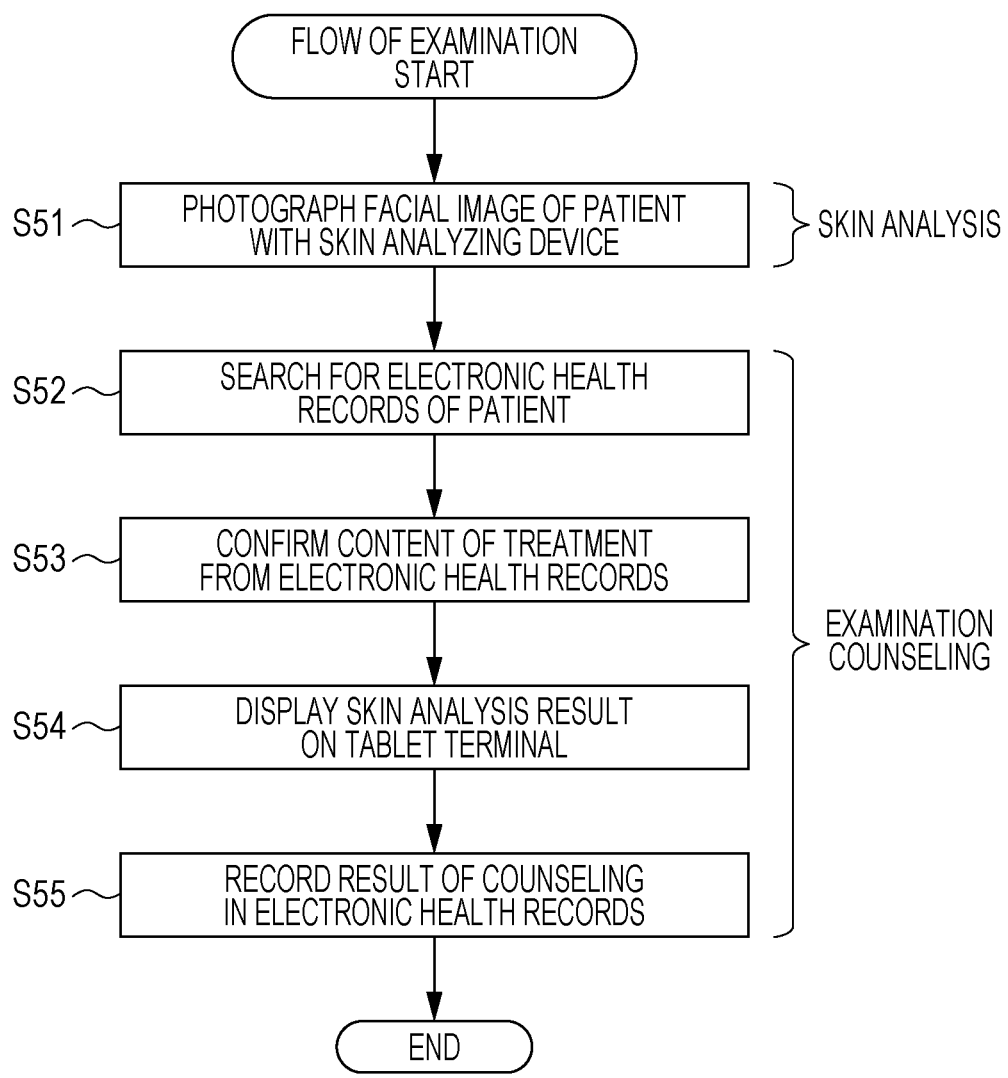
FIG. 13 is a flowchart illustrating an example of the flow of an examination using the cooperative system according to Embodiment 2.

According to these arrangements, a medical worker can reference the past results list UI 570 in S51 in FIG. 13 for example, and easily confirm points for photography in the skin analysis this time.

Details of Health Record UI Unit

Figure 17:
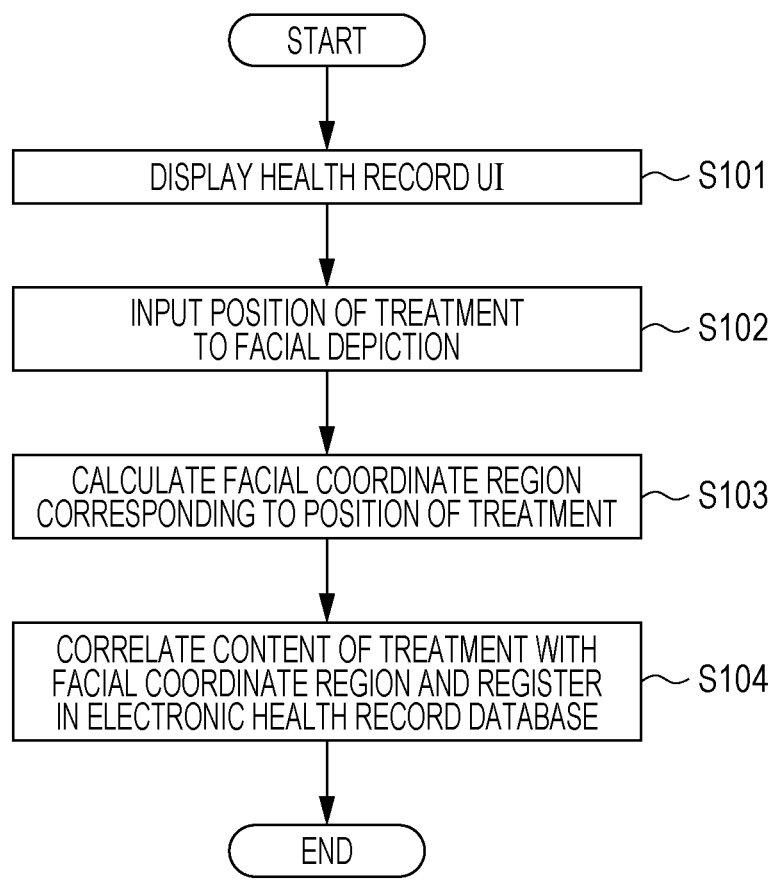
FIG. 17 is a flowchart illustrating an example of processing performed at a medical record UI unit according to Embodiment 2.

Next, the processing performed at the health record UI unit 301 will be described with reference to the flowchart illustrated in FIG. 17.

Figure 18:
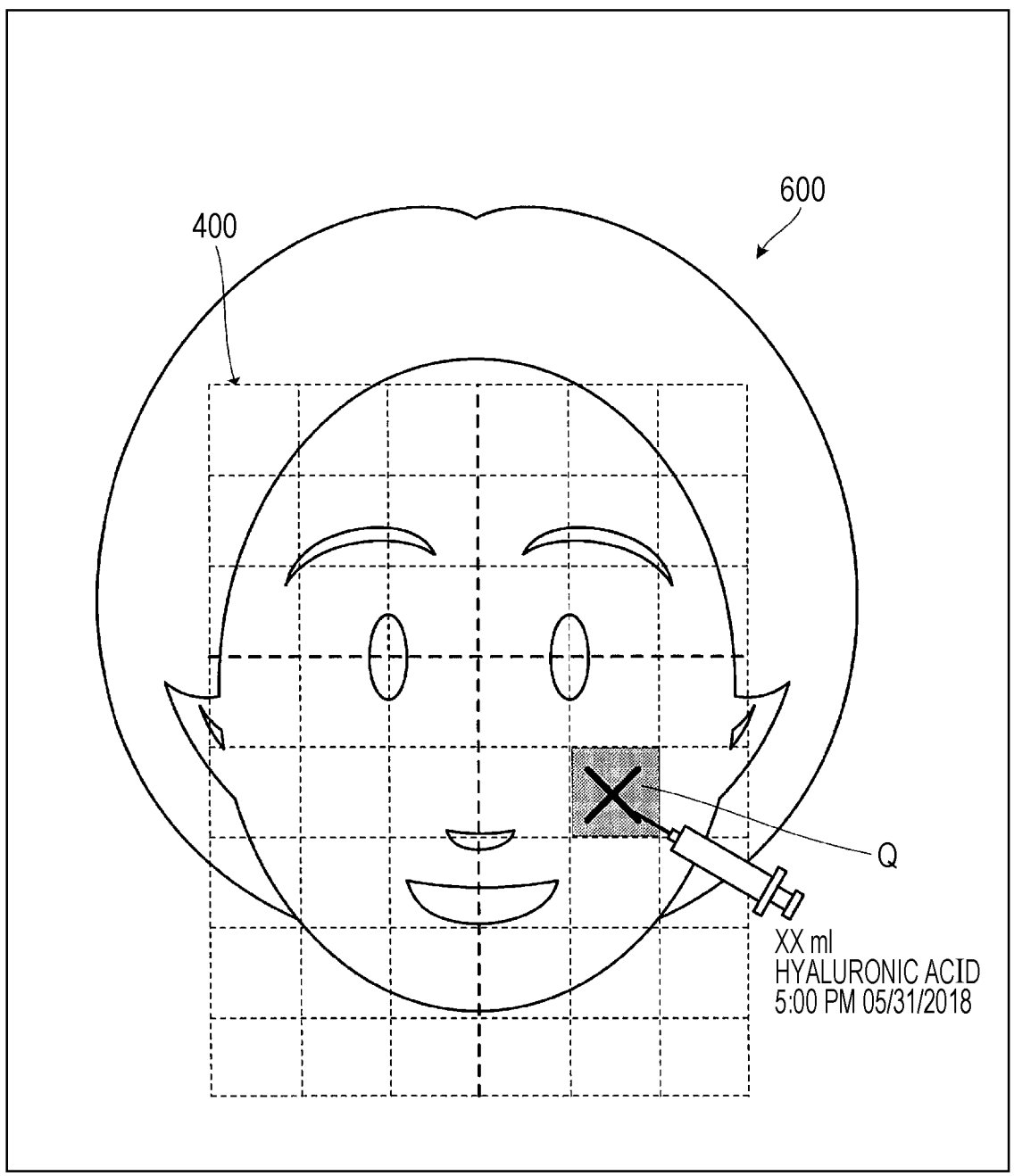
FIG. 18 is a diagram illustrating an example of a facial depiction according to Embodiment 2.

The health record UI unit 301 displays a health record UI including a facial depiction 600 such as exemplified in FIG. 18 (S101). The medical worker inputs patient information, date of treatment, content of treatment, and position of treatment, to the health record UI. Examples of patient information include the name of the patient, age, gender, hospital card No., and so forth. At this time, the medical worker inputs the position of treatment and content of treatment as to the facial depiction 600 exemplified in FIG. 18 (S102). Examples of the content of treatment include hyaluronic acid injection, laser resurfacing, and so forth.

The health record UI unit 301 uses the facial coordinates 400 set to the facial depiction 600 beforehand to calculate a facial coordinate region corresponding to the treatment position input in S102 (S103). Note that the facial coordinates 400 are also shown in FIG. 18 to facilitate description, but the facial coordinates 400 may be hidden from display in the health record UI.

The health record UI unit 301 stores the patient information and content of treatment input in S102, and the facial coordinate region corresponding to the treatment position calculated in S103, in the electronic health record database 40 in a correlated manner (S104).

According to the processing described above, an electronic health record correlated with the facial coordinate region corresponding to the position of treatment is stored in the electronic health record database 40.

Example of Electronic Health Record Cooperation

Next, examples B1, B2, B3, and B4 of cooperation between electronic health records stored in the electronic health record database 40 and skin analysis results stored in the skin analysis database 20, by the skin analyzing device 10, will be described.

Figure 19:
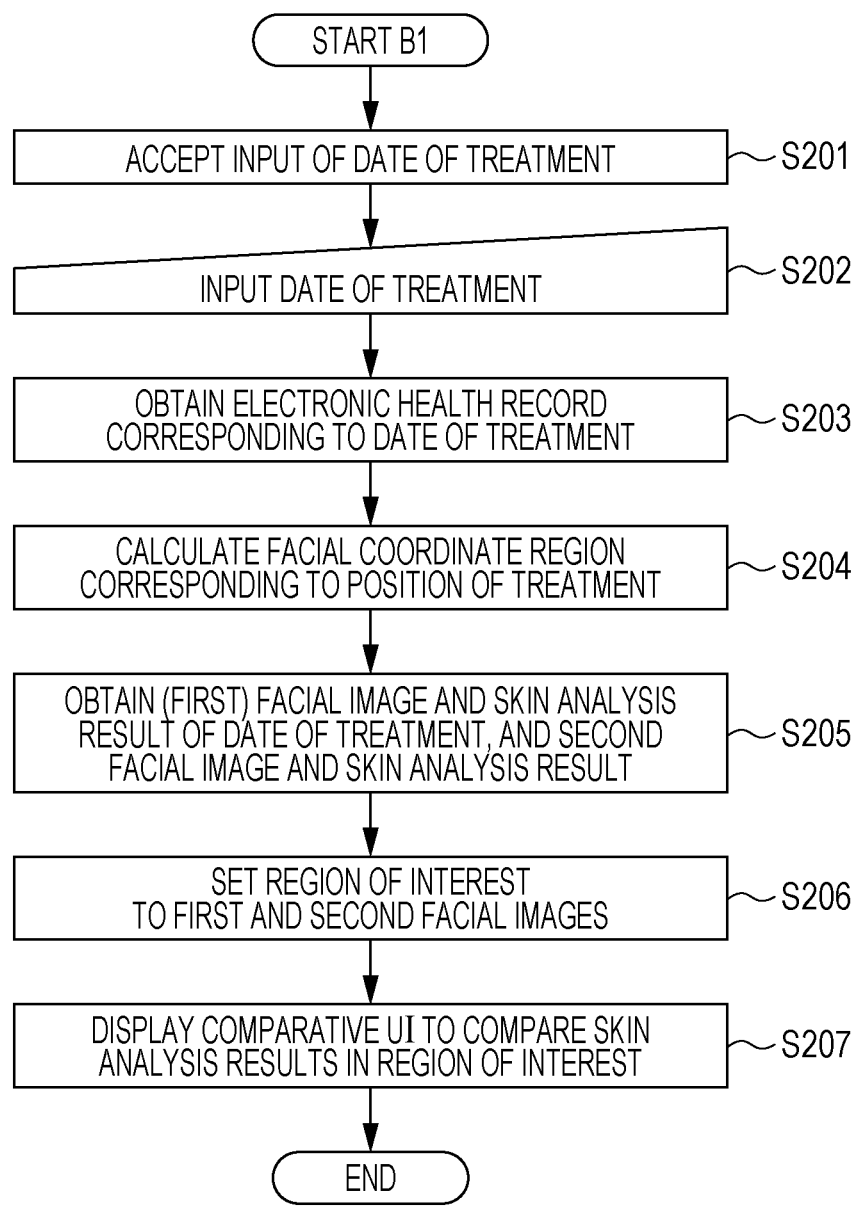
FIG. 19 is a flowchart illustrating a first example of processing according to Embodiment 2.

Example B1 will be described next with reference to the flowchart in FIG. 19.

The skin analysis UI unit 206 accepts input of the date of treatment, or which time of treatment (treatment at the first time, treatment at the second time, and so forth) (S201). The medical worker (operator) inputs date of treatment or which time of treatment for comparison (S202). Note that in a case of inputting which time of treatment, the skin analysis UI unit 206 identifies the date of treatment on which the treatment was performed that time.

The skin analysis UI unit 206 obtains the electronic health record corresponding to the date of treatment from S202, from the electronic health record database 40 (S203). The skin analysis UI unit 206 calculates a facial coordinate region corresponding to the position of treatment, from the electronic health record obtained in S203 (S204).

The skin analysis UI unit 206 obtains a facial image from the date of treatment from S202 (first facial image) and skin analysis result thereof (first skin analysis result), and a second facial image and second skin analysis result for comparison (S205), from the skin analysis database 20. Note that the second skin analysis result may be the newest skin analysis result, or may be the result selected by the operator.

The region-of-interest setting unit 207 sets a region of interest to a region corresponding to the facial coordinate region from S204, with regard to the first facial image and second facial image from S205 (S206). The size of this region of interest may be decided beforehand in accordance with the content of treatment recorded in the electronic health records. For example, in a case where the content of treatment is "hyaluronic acid injection", the size of the region of interest may be decided beforehand to be 3 cm in diameter.

The skin analysis UI unit 206 displays a comparative UI comparing the first skin analysis result and the second skin analysis result in the region of interest from S205 (S207). This comparative UI may be any comparative UI described in Embodiment 1.

According to this example B1, the medical worker (operator) and patient who has received treatment (measurement subject) can quickly and easily compare effects of the treatment at the position of treatment from the comparative UI.

Figure 20:
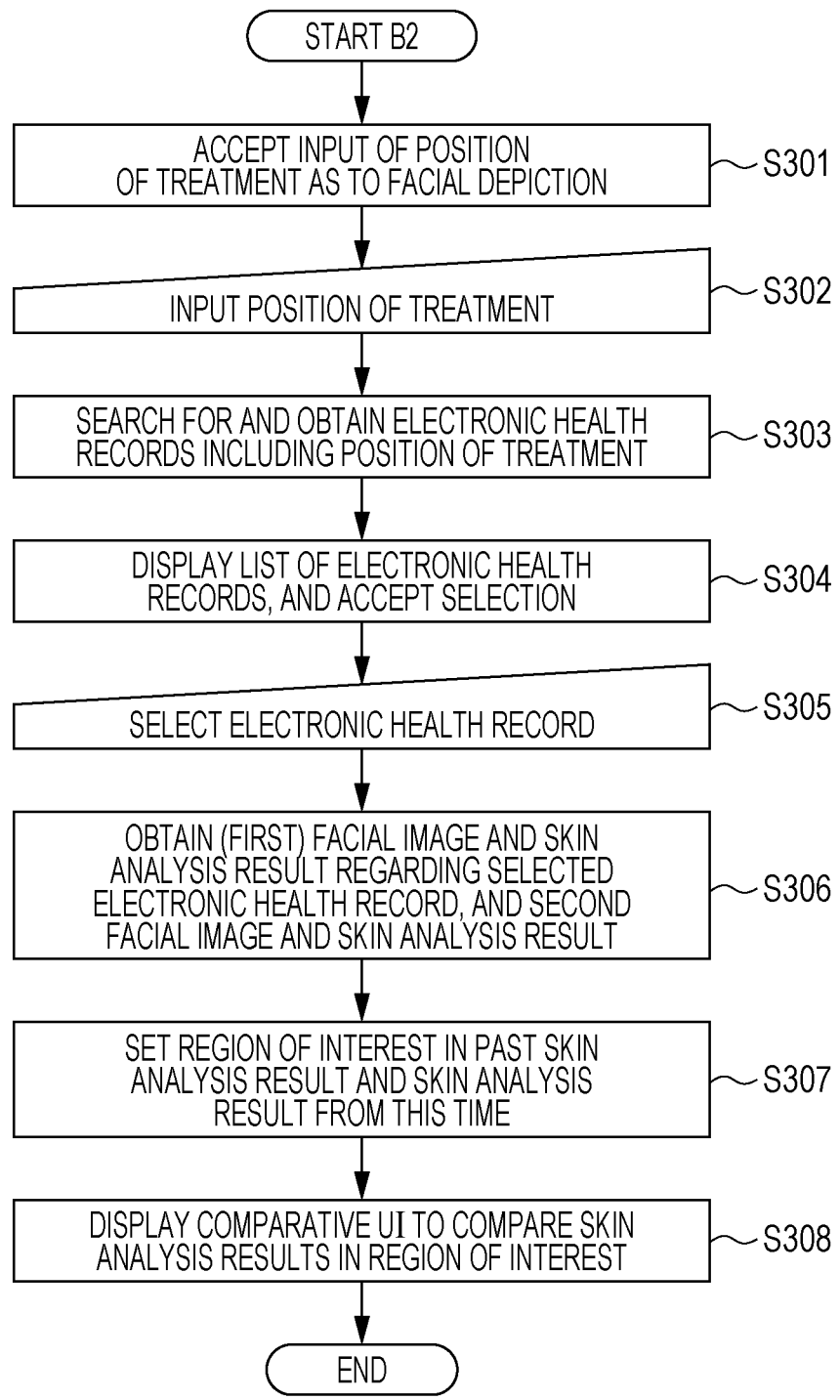
FIG. 20 is a flowchart illustrating a second example of processing according to Embodiment 2.

Next, example B2 will be described with reference to the flowchart in FIG. 20.

Figure 21:
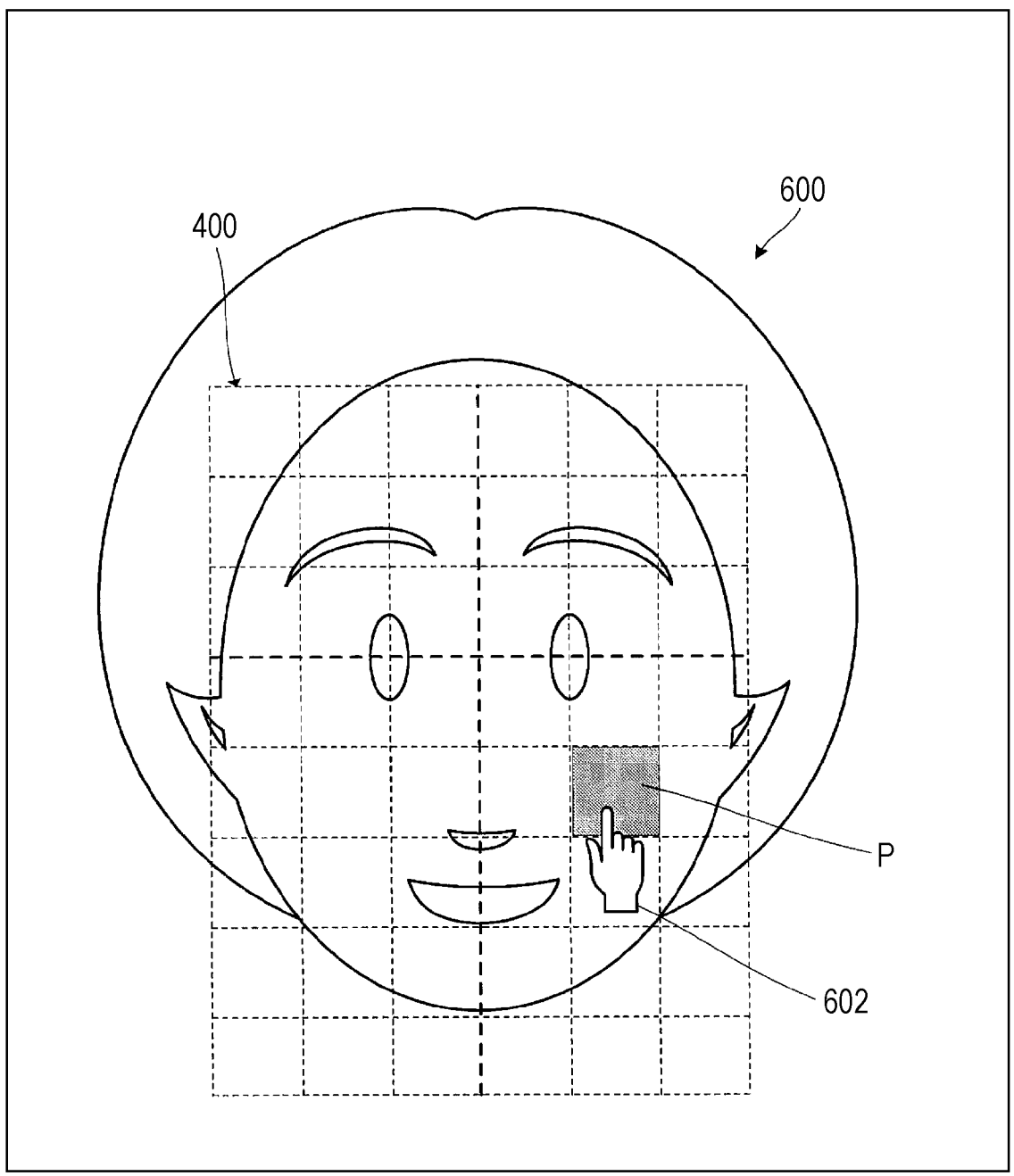
FIG. 21 is a diagram illustrating an example of a facial depiction in the second example of processing according to Embodiment 2.

The skin analysis UI unit 206 displays a facial depiction 600 such as exemplified in FIG. 21, and accepts input of a position of treatment as to the facial depiction 600 (S301).

A medical worker (operator) operates a finger icon 602, for example, and inputs a position of treatment of the measurement subject as to the facial depiction 600 (S302).

The skin analysis UI unit 206 searches for and obtains electronic health records of measurement subjects including the position of treatment from S302, from the electronic health record database 40 (S303).

The skin analysis UI unit 206 displays a list of electronic health records obtained in S303, and accepts selection of an electronic health record (S304). The operator selection one electronic health record from the list of electronic health records (S305).

The skin analysis UI unit 206 obtains, from the control unit 20, a facial image relating to the electronic health record selected in S305 (first facial image) and skin analysis result thereof (first skin analysis result) of the day of treatment, and a second facial image and second skin analysis result for comparison (S306). Note that the second skin analysis result may be the newest skin analysis result, or may be the result selected by the medical worker.

The region-of-interest setting unit 207 sets a region of interest to the facial coordinate region corresponding to the treatment position input to the facial depiction 600, with regard to the first facial image and second facial image (S307). The region-of-interest setting unit 207 may decide the size of this region of interest in accordance with the content of treatment recorded in the electronic health record selected in S305.

The skin analysis UI unit 206 displays a comparative UI comparing the first skin analysis result and the second skin analysis result in the region of interest from S307 (S308). This comparative UI may be any comparative UI described in Embodiment 1.

According to this example B2, the medical worker (operator) and patient (measurement subject) can quickly and easily compare the state of the skin immediately after treatment and the newest state of the skin, at the treatment position, from the comparative UI. For example, whether or not there is an increase in wrinkles around the eyes where treatment was performed one year ago, can easily be compared.

Figure 22:
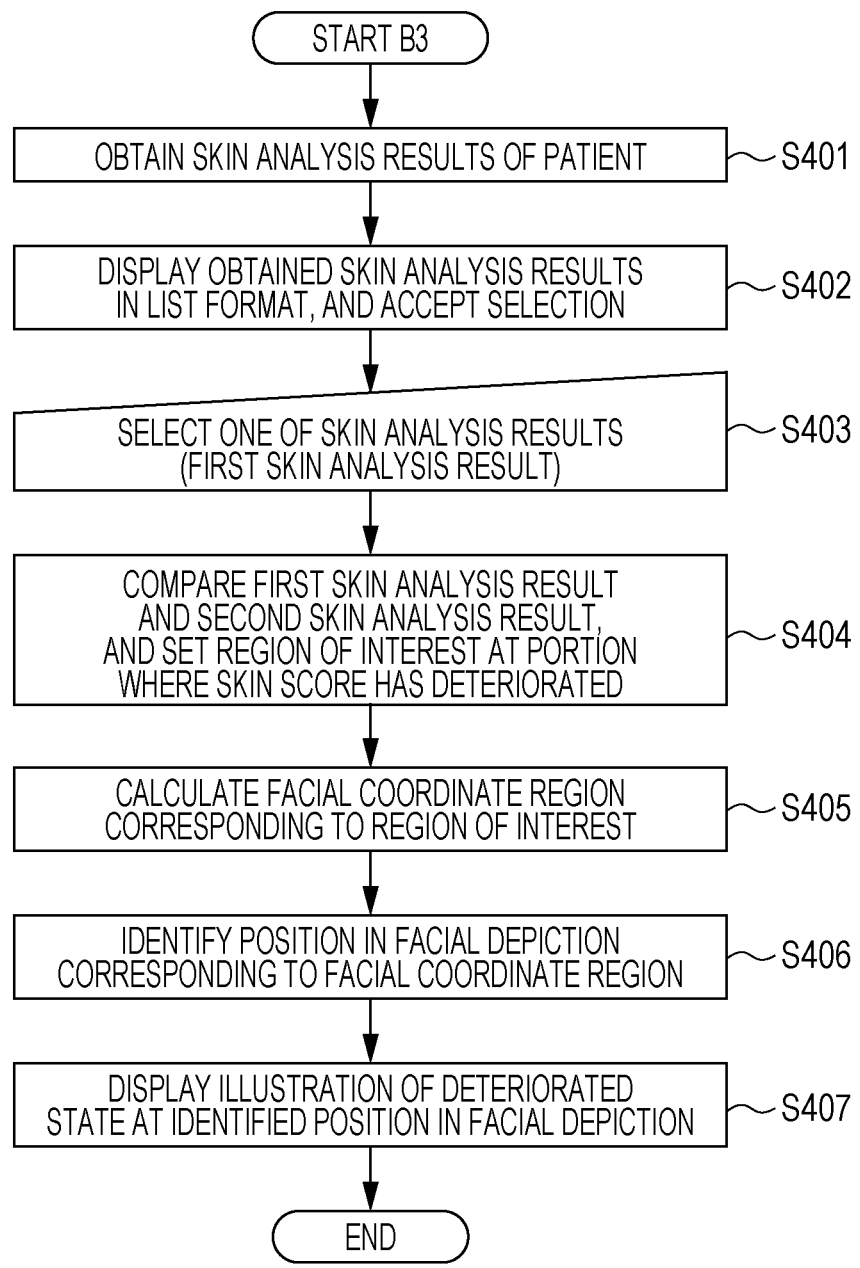
FIG. 22 is a flowchart illustrating a third example of processing according to Embodiment 2.

Next, example B3 will be described with reference to the flowchart in FIG. 22.

The skin analysis UI unit 206 obtains skin analysis results of a patient from the skin analysis database 20 (S401). The skin analysis UI unit 206 displays the obtained skin analysis results in a list format, and accepts selection of a skin analysis result (S402). The medical worker (operator) selects one of the skin analysis results from the list (S403).

The region-of-interest setting unit 207 compares the skin analysis result selected in S402 (first skin analysis result) with second skin analysis result for comparison, and sets a region of interest at a portion where the skin score is deteriorated most from the entire face (S404). Note that the second skin analysis result may be the newest skin analysis result, or may be the result selected by the medical worker.

The region-of-interest setting unit 207 calculates a facial coordinates region P corresponding to that region of interest (S405). The region-of-interest setting unit 207 identifies the position on the facial depiction 600 corresponding to the facial coordinates region P from S404 (S406).

Figure 23:
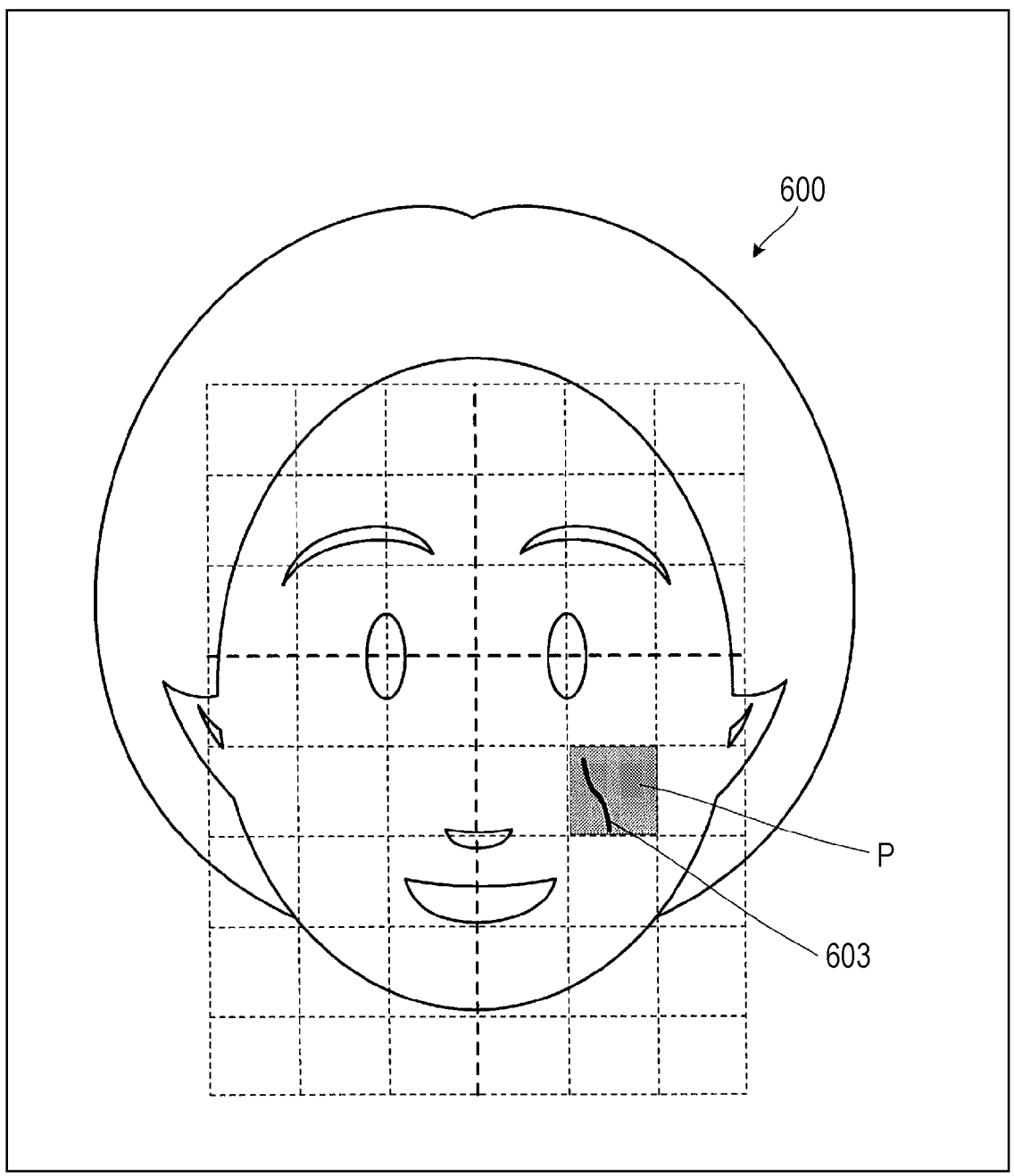
FIG. 23 is a diagram illustrating an example of a facial depiction in the third example of processing according to Embodiment 2.

The skin analysis UI unit 206 displays an illustration 603 illustrating a deteriorated state at the position of the facial depiction 600 identified in S404 (S407), as exemplified in FIG. 23. For example, the skin analysis UI unit 206 displays an illustration 603 of a skin analysis object that has deteriorated in the region of interest (e.g., an increase in wrinkles).

According to this example B3, the medical worker (operator) and patient (measurement subject) can quickly and easily recognize a portion where the skin condition has deteriorated, from the facial depiction 600 where the illustration 603 indicating a deteriorated state has been drawn.

Figure 24:
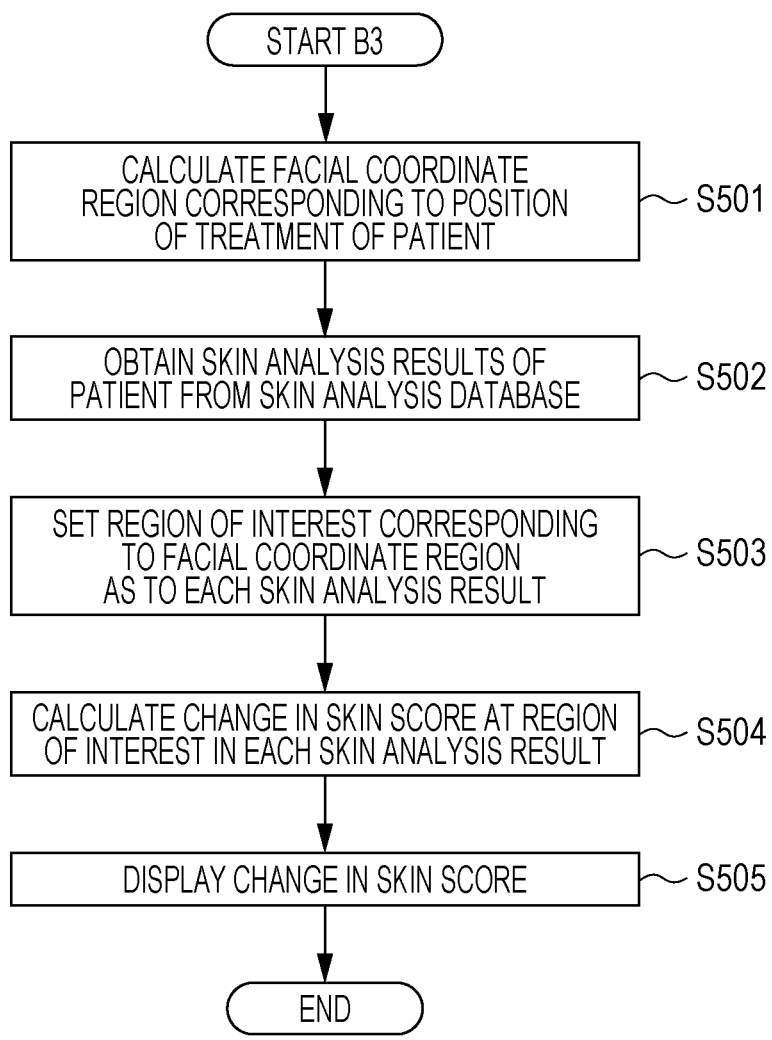
FIG. 24 is a flowchart illustrating a fourth example of processing according to Embodiment 2.

Next, example B4 will be described with reference to the flowchart in FIG. 24.

The region-of-interest setting unit 207 calculates a facial coordinates region corresponding to the treatment position of the patient (S501). Note that the treatment position may have been recorded in electronic health records. Alternatively, the treatment position maybe input to the facial depiction 600 by the medical worker (operator).

The region-of-interest setting unit 207 obtains skin analysis results of the patient from the skin analysis database 20 (S502). The region-of-interest setting unit 207 sets a region of interest corresponding to the facial coordinates region in each of the skin analysis results (S503).

The skin analysis UI unit 206 calculates change in the skin score at the region of interest in each of the skin analysis results (S504).

The skin analysis UI unit 206 displays change in the skin score from S504 (S505). Note that the skin analysis UI unit 206 may display the relation between change in the skin score and the number of times of having received treatment. For example, in a case where the skin score in the region of interest has improved from the fourth treatment, the skin analysis UI unit 206 may display "improved since fourth treatment".

According to this example B4, the medical worker (operator) and patient (measurement subject) can quickly and easily recognize change in the condition of skin at portions that have received treatment.

Embodiment 3

Effects of treatment of the skin may be manifested after having performed treatment multiple times. Accordingly, a skin analyzing device 10 that can predict a skin analysis result of the patient after treatment, based on results of having statistically analyzed a great number of skin analysis results as to content of treatment, will be described in Embodiment 3.

Figure 25:
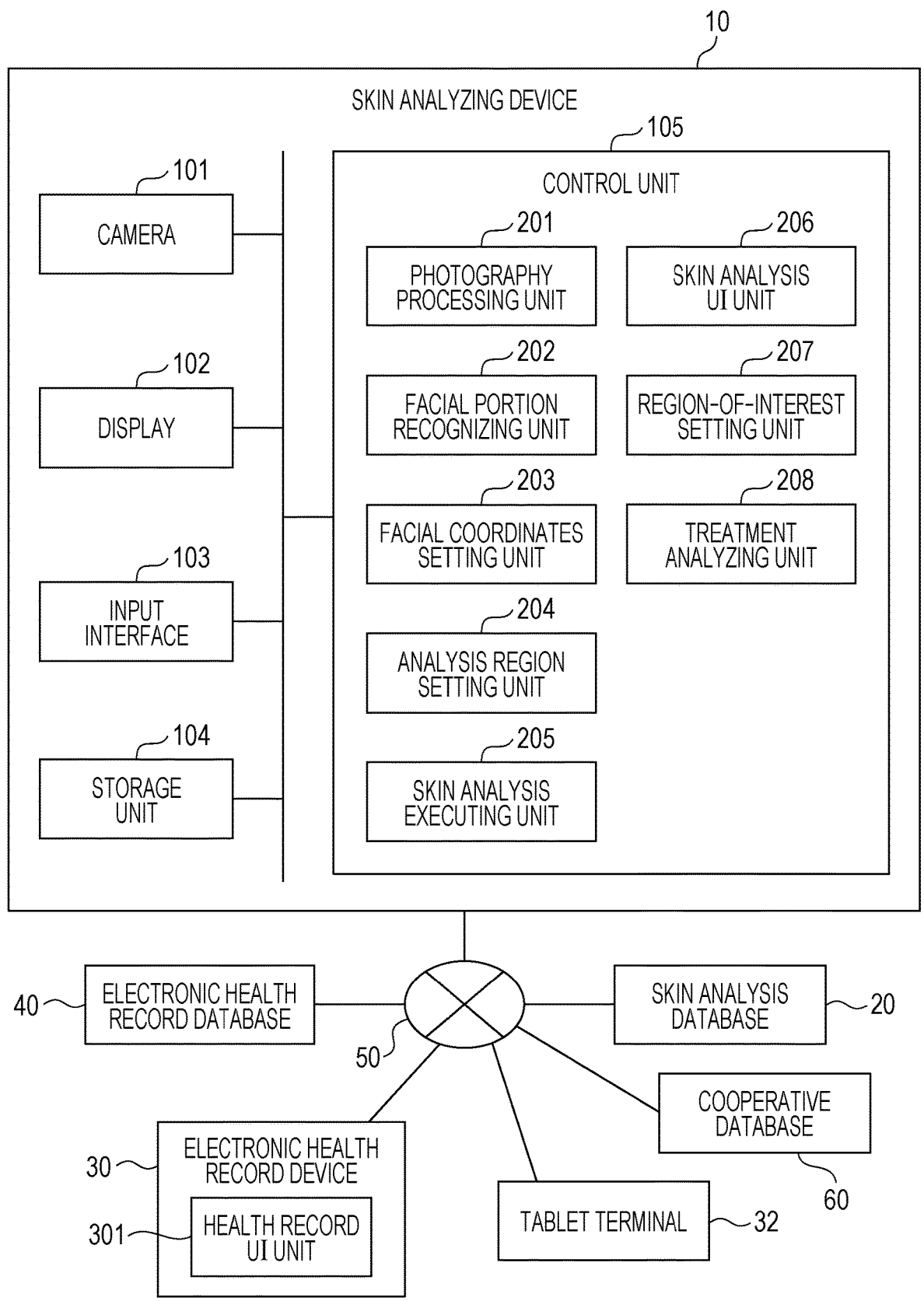
FIG. 25 is a diagram illustrating a configuration example of a cooperative system according to Embodiment 3.

FIG. 25 illustrates a configuration example of a cooperative system according to Embodiment 3. Components that are the same as those in FIG. 3 or 12 may be denoted by the same reference numerals and description thereof be omitted.

The cooperative system according to Embodiment 3 has, in addition to the components illustrated in FIG. 12, a cooperative database 60. The cooperative database 60 is connected to the communication network 50, and is capable of exchanging data with the skin analyzing device 10 and electronic health record device 30. Note that details of the cooperative database 60 will be described later in "Details of Cooperative Database".

Figure 3:
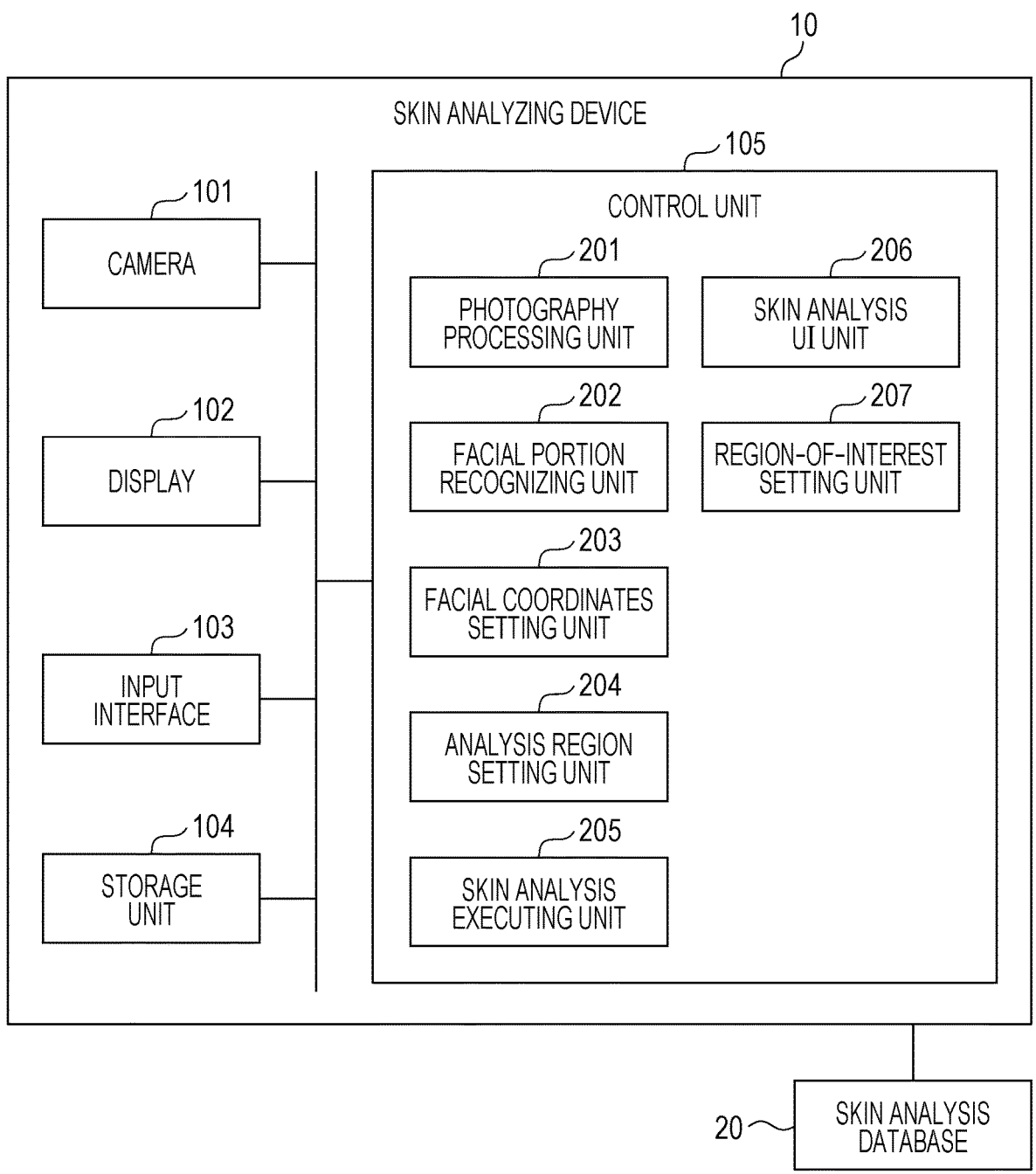
FIG. 3 is a diagram illustrating a configuration example of the skin analyzing device according to Embodiment 1.

The skin analyzing device 10 also has, in addition to the components illustrated in FIG. 3 or 12, a treatment analyzing unit 208. The treatment analyzing unit 208 references electronic health records in the electronic health record database 40 and skin analysis results in the skin analysis database 20, correlates the content of treatment with the skin analysis result following the treatment, and stores in the cooperative database 60. The treatment analyzing unit 208 uses multiple skin analysis results in the cooperative database 60, to calculate correlation between the number of times of treatment and the skin analysis results. Note that details of the treatment analyzing unit 208 will be described later in "Details of Treatment Analyzing Unit".

Details of Cooperative Database

FIG. 26 illustrates a configuration example of the cooperative database 60.

The cooperative database 60 manages a plurality of cooperative information. Data items of cooperative information are patient attributes, date of treatment, content of treatment, treatment position, number of times of treatment, and skin score.

Patient attributes is information indicating attributes of the patient, such as gender, age, and so forth, of the patient. Date of treatment is information indicating the date on which treatment was performed. Content of treatment is information indicating the content of treatment performed on the date of treatment. Treatment position is information indicating the position on the face where treatment according to the content of treatment was performed. The number of times of treatment is information indicating the number of times that treatment has been performed at the position of treatment. Skin score is information indicating a skin score measured after treatment according to the content of treatment has been performed. Skin score may be a skin score for each skin analysis object, such as blemishes, wrinkles, pores, and so forth.

Details of Treatment Analyzing Unit

Figure 27:
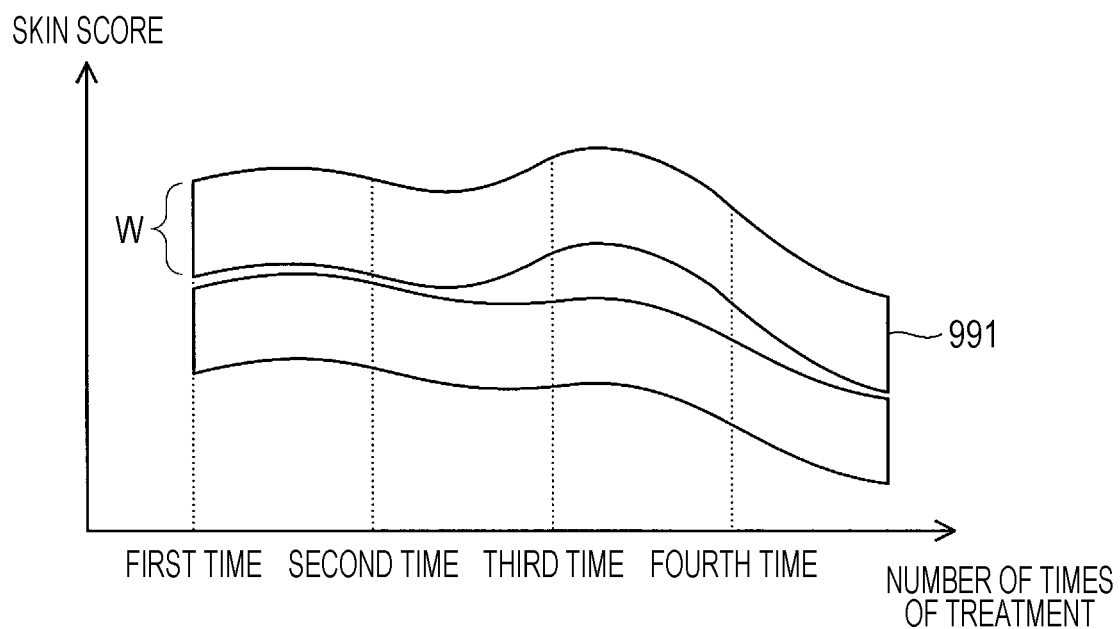
FIG. 27 is a diagram illustrating an example of correlation between the number of times of treatment and a skin score according to Embodiment 3.

FIG. 27 is a graph indicating a statistical skin score for each time treatment was performed.

The treatment analyzing unit 208 uses multiple sets of cooperative information in the cooperative database 60 to calculate a statistical skin score 991 for each time of treatment. For example, an n'th-time (where n is an integer of 1 or more) statistical skin score 991 may be an average value of n'th skin scores of multiple patients that have received the same treatment. Also, the statistical skin score 991 may be a value indicating a range W, as illustrated in FIG. 27. This range may be calculated based on a variance value of multiple skin scores.

The treatment analyzing unit 208 may group cooperative information having common patient attributes (e.g., women in their forties, or the like), and calculate a statistical skin score 991 for each group. The treatment analyzing unit 208 may calculate statistical skin scores 991 for the region of interest.

Figure 28:
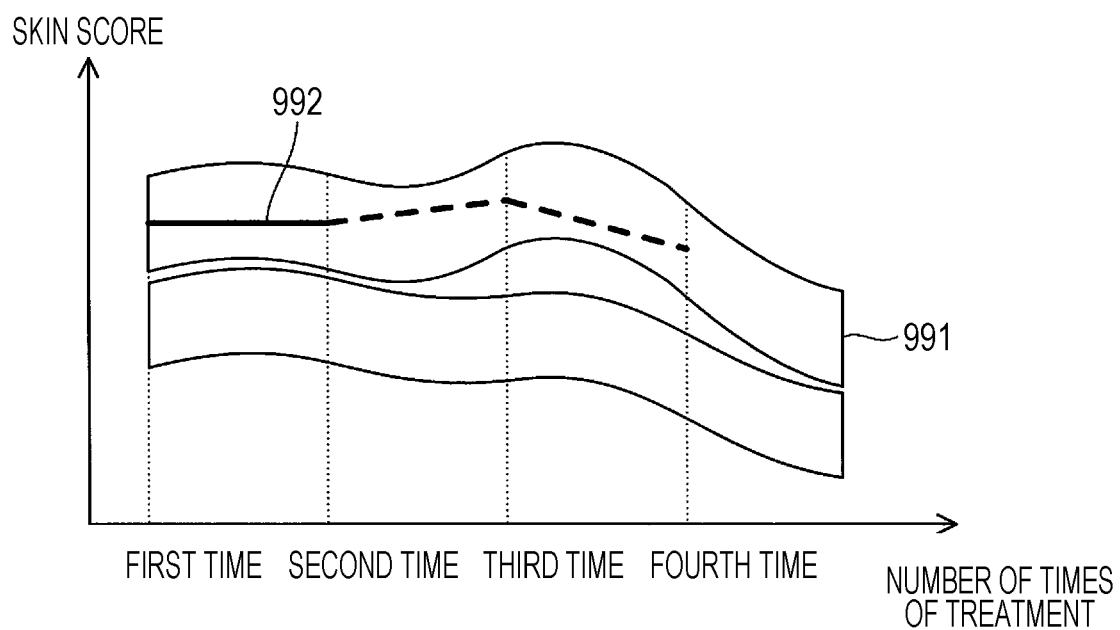
FIG. 28 is a diagram illustrating an example of prediction of skin score after treatment according to Embodiment 3.

FIG. 28 is a graph illustrating prediction values of skin scores after treatment of a patient.

The treatment analyzing unit 208 uses the statistical skin score 991 from each time of treatment to predict change in skin score 992 of a patient, regarding a case where the patient receives treatment in the future. For example, the treatment analyzing unit 208 assumes that actual values (solid line) of the skin score 992 after the first and second treatments of the patient will trend in the same way as the statistical skin score 991, and calculates prediction values (dashed line) of the skin score 992 regarding a case of this patient if receiving third and fourth treatments in the future, as illustrated in FIG. 28.

Accordingly, the medical worker (operator) and patient (measurement subject) can predict the number of times of treatment where the effects of treatment will be greatest.

Summarization of Present Disclosure

The skin analyzing device 10 according to the present disclosure includes the facial coordinates setting unit 203 that sets facial coordinates on a facial image of a measurement subject by using, as a reference, by using a position of a facial portion identified from the facial image, the region-of-interest setting unit 207 that sets a first region of interest to a first facial image of the measurement subject, and sets a second region of interest that has facial coordinates in common with the first region of interest to a second facial image of the measurement subject, and the skin analysis UI unit 206 that displays the first facial image and the second facial image next to each other, and displays a skin analysis result in the first region of interest with respect to the first facial image, and a skin analysis result in the second region of interest with respect to the second facial image.

Thus, by setting facial coordinates based on a facial portion with respect to two facial images of a measurement subject, setting a common region of interest in facial coordinates for each of the two facial images, and displaying skin analysis results at the region of interest next to each other, change in skin condition of the substantially common region of interest can easily be recognized, even if the two facial images are taken at different timings.

Figure 29:
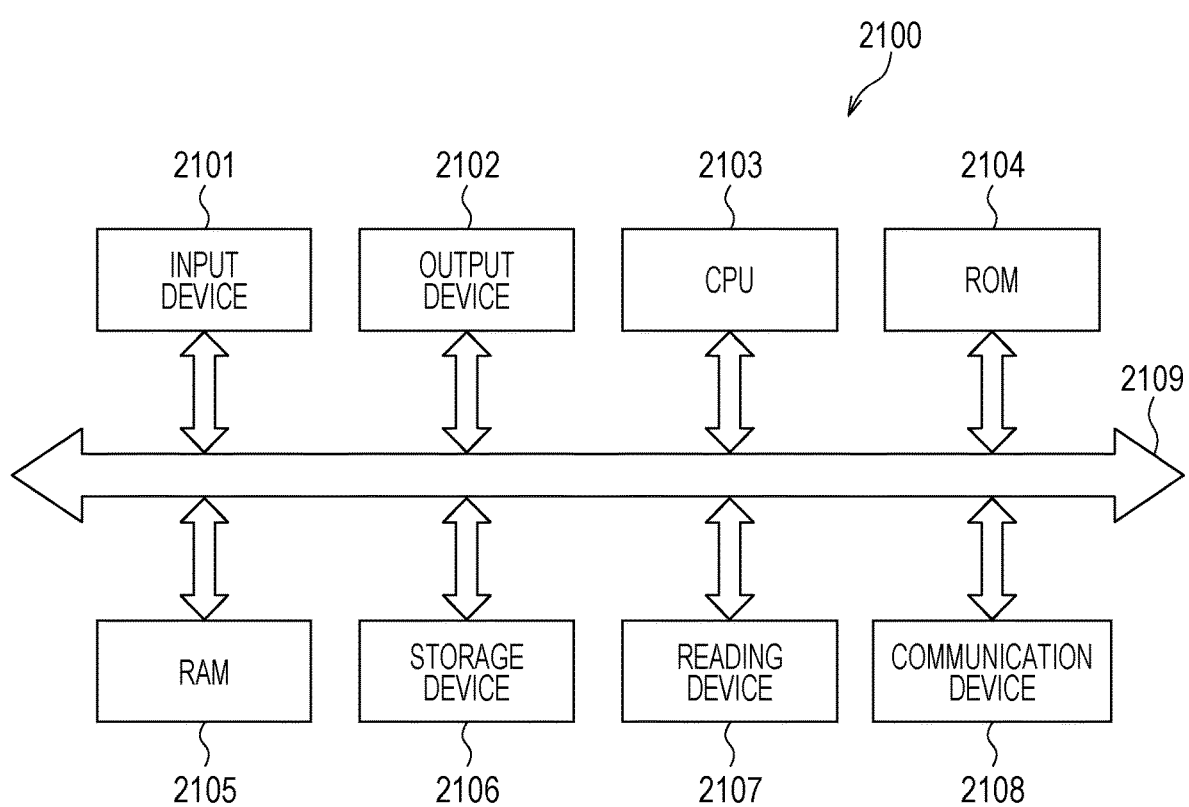
FIG. 29 is a diagram illustrating an example of a hardware configuration according to the present disclosure.

FIG. 29 is a diagram illustrating a hardware configuration of a computer that realizes functions of the devices by a program. This computer 2100 has an input device 2101 such as a keyboard, mouse, touchpad, or the like, an output device 2102 such as a display, speaker, or the like, a central processing unit (CPU) 2103, read only memory (ROM) 2104, random access memory (RAM) 2105, a storage device 2106 such as a hard disk device or solid state drive (SSD) or the like, a reading device 2107 that reads information from a storage medium such as digital versatile disk read only memory (DVD-ROM) or Universal Serial Bus (USB) memory or the like, and a communication device 2108 that performs communication via a network, each part being connected by a bus 2109.

The reading device 2107 then reads, from a recording medium storing the program for realizing the functions of the above devices, that program, and stores in the storage device 2106. Alternatively, the communication device 2108 performs communication with a server device connected to a network, and stores in the storage device 2106 the program for realizing the functions of the above devices that has been downloaded from the server device.

The CPU 2103 copies the program stored in the storage device 2106 to the RAM 2105, sequentially reads out from the RAM 2105 and executes commands included in the program, whereby the functions of the above devices are realized.

The present disclosure can be realized by software, hardware, or software in cooperation with hardware.

The functional blocks such as used in the above-described embodiments may be partly or fully realized as large scale integration (LSI) that is an integrated circuit, and the processes described in the above embodiments may be partially or entirely controlled by one LSI or a combination of LSIs. These LSIs may be individually formed into one chip, or part or all of the functional blocks may be included in one chip. LSIs may have data input and output. There are different names of LSIs such as IC, system LSI, super LSI, and ultra LSI, depending on the degree of integration.

The circuit integration technique is not restricted to LSIs, and dedicated circuits, general-purpose processors, or dedicated processors may be used to realize the same. A field programmable gate array (FPGA) which can be programmed after manufacturing the LSI, or a reconfigurable processor where circuit cell connections and settings within the LSI can be reconfigured, may be used. The present disclosure may be realized by digital processing or analog processing.

Further, in the event of the advent of an integrated circuit technology which would replace LSIs by advance of semiconductor technology or a separate technology derived therefrom, such a technology may be used for integration of the functional blocks, as a matter of course. Application of biotechnology and so forth is a possibility.

One form of the present disclosure is useful in a skin analyzing system.

What is claimed is:

1. A skin analyzing device, comprising:
  a processor configured to
    set facial coordinates on a facial image of a measurement subject by using, as a reference, a position of a facial portion identified from the facial image;
    set a first region of interest on a first facial image of the measurement subject, and
    set a second region of interest on a second facial image of the measurement subject; and
  a skin analysis user interface configured to
    (i) display the first facial image and the second facial image next to each other, and
    (ii) display a skin analysis result in the first region of interest with respect to the first facial image, and a skin analysis result in the second region of interest with respect to the second facial image, wherein
  the second region of interest has facial coordinates in common with the first region of interest, and the processor is also configured to set the facial coordinates using the center of a straight line connecting the right eye and the left eye in the facial image of the measurement subject.

2. The skin analyzing device according to claim 1, wherein
the skin analysis result is a count of pores, an area size of a blemish, a darkness of a blemish, an area size of wrinkles, or a depth of wrinkles, and
the skin analysis user interface is configured
to perform drawing in the first region of interest on the first facial image in accordance with the skin analysis result in the first region of interest, and
to perform drawing in the second region of interest on the second facial image in accordance with the skin analysis result in the second region of interest.

3. The skin analyzing device according to claim 1, wherein the processor is also configured
to obtain, from a predetermined database, electronic health record information including content of treatment that the measurement subject received on the face, and a position of the treatment, and
to set the first and second regions of interest on the first and second facial images respectively at a position that is in common in the facial coordinates with the position of the treatment in the electronic health record information.

4. The skin analyzing device according to claim 3, wherein the processor is also configured to determine a size of the first and second regions of interest in accordance with the skin analysis result or the content of the treatment.

5. The skin analyzing device according to claim 1, wherein the processor is also configured
to compare a skin analysis result of an entirety of the first facial image and a skin analysis result of an entirety of the second facial image, and
to set a region where change in the skin analysis results is greatest, in the first and second regions of interest.

6. A skin analyzing method by a skin analyzing device, the method comprising:
setting facial coordinates on a facial image of a measurement subject by using, as a reference, a position of a facial portion identified from the facial image;
setting a first region of interest on a first facial image of the measurement subject;
setting sets a second region of interest that has facial coordinates in common with the on a second facial image of the measurement subject;
displaying the first facial image and the second facial image next to each other; and
displaying a skin analysis result in the first region of interest with respect to the first facial image, and a skin analysis result in the second region of interest with respect to the second facial image, wherein
the second region of interest has facial coordinates in common with the first region of interest, and
the setting of the facial coordinates uses the center of a straight line connecting the right eye and the left eye in the facial image.

7. A computer-readable recording medium storing a program to be executed by a skin analyzing device, the program causing a computer of the skin analyzing device to execute
setting facial coordinates on a facial image of a measurement subject by using, as a reference, a position of a facial portion identified from the facial image,
setting a first region of interest on to a first facial image of the measurement subject, sets
setting a second region of interest on a second facial image of the measurement subject,
displaying the first facial image and the second facial image next to each other, and
displaying a skin analysis result in the first region of interest with respect to the first facial image, and a skin analysis result in the second region of interest with respect to the second facial image, wherein
the second region of interest has facial coordinates in common with the first region of interest, and
the setting of the facial coordinates uses the center of a straight line connecting the right eye and the left eye in the facial image.

8. The skin analyzing device according to claim 2, wherein the processor is also configured
to obtain, from a predetermined database, electronic health record information including content of treatment that the measurement subject received on the face, and a position of the treatment, and
to set the first and second regions of interest on the first and second facial images respectively at a position that is in common in the facial coordinates with the position of the treatment in the electronic health record information.

9. The skin analyzing device according to claim 8, wherein the processor is also configured to determine a size of the first and second regions of interest in accordance with the skin analysis result or the content of the treatment.

10. The skin analyzing device according to claim 2, wherein the processor is also configured
to compare a skin analysis result of an entirety of the first facial image and a skin analysis result of an entirety of the second facial image, and
to set a region where change in the skin analysis results is greatest, in the first and second regions of interest.

* * * * *